US008808670B2

(12) United States Patent
Döring et al.

(10) Patent No.: US 8,808,670 B2
(45) Date of Patent: *Aug. 19, 2014

(54) COSMETIC AND DERMATOLOGICAL PHOTOPROTECTIVE FORMULATIONS

(75) Inventors: Thomas Döring, Dormagen (DE); Martin Sugár, Hamburg (DE); Rainer Wolber, Hamburg (DE); Volker Wendel, Frankfurt am Main (DE); Thomas Blatt, Wedel (DE); Claudia Mundt, Bremen (DE); Jens Schulz, Schenefeld (DE); Jan Batzer, Hamburg (DE); Rixa Dippe, Hamburg (DE)

(73) Assignee: Beiersdorf AG, Hamburg (DE)

( * ) Notice: Subject to any disclaimer, the term of this patent is extended or adjusted under 35 U.S.C. 154(b) by 575 days.

This patent is subject to a terminal disclaimer.

(21) Appl. No.: 11/087,395

(22) Filed: Mar. 23, 2005

(65) Prior Publication Data
US 2006/0008426 A1    Jan. 12, 2006

(30) Foreign Application Priority Data

Mar. 23, 2004   (DE) .......................... 10 2004 014 614
Apr. 27, 2004   (DE) .......................... 10 2004 020 627

(51) Int. Cl.
*A61K 8/00*         (2006.01)
(52) U.S. Cl.
USPC ........................................................ 424/59

(58) Field of Classification Search
USPC ............................................................ 424/59
See application file for complete search history.

(56) References Cited

U.S. PATENT DOCUMENTS

| 5,091,171 | A  | * | 2/1992 | Yu et al. ........................ 424/642 |
| 6,514,485 | B1 | * | 2/2003 | Malpede et al. ................ 424/59 |
| 2005/0008587 | A1 | | 1/2005 | Schulz et al. |
| 2005/0013782 | A1 | | 1/2005 | Göppel et al. |
| 2005/0025726 | A1 | | 2/2005 | Göppel et al. |
| 2005/0048009 | A1 | | 3/2005 | Göppel et al. |

FOREIGN PATENT DOCUMENTS

| DE | 101 40 537 A1 | 2/2003 |
| DE | 101 55 962 A1 | 5/2003 |
| DE | 101 55 965 A1 | 5/2003 |
| DE | 102 14 059 A1 | 10/2003 |
| DE | 102 26 353 A1 | 12/2003 |
| WO | WO 03/053390 A1 | 7/2003 |

OTHER PUBLICATIONS

Wendel et al., Photodermatology Photoimmunology and PhotoMedicine, 2003, 93-97.*
Ferrero et al., 2002, International Journal of Cosmetic Science, 24, 63-70.*
Wendel et al., SOFW-Journal, 2001, 27, pp. 12, 14-16 and 29-30.*

* cited by examiner

*Primary Examiner* — Abigail Fisher
(74) *Attorney, Agent, or Firm* — Abel Law Group, LLP

(57) ABSTRACT

Cosmetic or dermatological preparations which have a UVA balance of more than 15, and use thereof.

31 Claims, No Drawings

COSMETIC AND DERMATOLOGICAL PHOTOPROTECTIVE FORMULATIONS

BACKGROUND OF THE INVENTION

The present invention relates to cosmetic and dermatological preparations with a high UVA balance, and to the use of such preparations for increasing and/or improving the natural, endogenous UV protection system, the skin moisture and the deep moisture of the skin, the vitality and the protection of skin cells, and the use for protecting the skin against premature aging and optically perceptible changes.

The harmful effect of the ultraviolet part of solar radiation on the skin is generally known. Depending on their particular wavelength, the rays have various effects on the skin organ:

The so-called UV-C radiation with a wavelength between 100 and 280 nm is absorbed by the ozone layer in the earth's atmosphere and accordingly is not found in the solar spectrum. It is therefore of no physiological significance during sunbathing.

The so-called UV-B region is between 290 nm and 320 nm. UV-B rays are essentially responsible for the long-lasting tanning of the skin, but can at the same time cause an erythema, simple sunburn or even burns of varying severity. Chronic photodamage, photodermatoses and Herpes solaris and skin cancer can also be caused by UV-B radiation.

Since sunburn is a typical UV-B effect, many cosmetic or dermatological photoprotective products comprise UV-B filter substances as essential constituents for protecting, in particular, against sunburn. To protect against UV-B radiation, numerous compounds are known whose absorption maximum should as far as possible be around 308 nm since it is here that the erythema effectiveness of solar radiation is highest. Typical UV-B filters are, for example, derivatives of 3-benzylidenecamphor, of 4-aminobenzoic acid, of cinnamic acid, of salicylic acid, of benzophenone, and also of 2-phenylbenzimidazole.

As already explained, skin tanning is also stimulated in particular by UV-B light. Here, the melanocytes in the skin form increased melanin, which ultimately constitutes the brown coloration. This so-called delayed tanning (DT), which is generally the desired tanning, is relatively long-lasting and, moreover, also represents an endogenous UV protection.

Photoprotective products with a content of UV-B filter substances thus protect not only against sunburn, but, moreover, particularly in the case of a high sun protection factor, also slow the development of natural skin tanning.

It has for a long time been incorrectly assumed that the long-wave UV-A radiation with a wavelength between 320 nm and 400 nm has only a negligible biological effect and that, accordingly, the UV-B rays are responsible for most photodamage to the human skin. However, in the meantime, numerous studies have demonstrated that UV-A radiation is much more harmful than UV-B radiation with regard to the triggering of photodynamic, specifically phototoxic, reactions and chronic changes in the skin. The harmful effect of UV-B radiation can also be further intensified by UV-A radiation.

Moreover, much of the damage which has previously typically been attributed to UV-B light is also found following exposure to UV-A light. Thus, for example, restrictions of the cellular vitality (which can also be referred to as "cell performance" or homeostasis of the cell physiology etc.) are to be attributed to UV light generally, but particularly to UV-A light. Inter alia, in addition the subcellular organization of the cytoskeleton is also severely impaired by UV light and thus reduces the "cellular firming" of the skin. In addition, on a cellular level, the effect of UV radiation results in a large amount of damage which has to be overcome by regeneration and repair both at a protein level and also at DNA level.

In addition, sunbathing and/or exposure to sun also lead to a drying-out of the skin. This drying-out can be superficial in nature and predominantly affect the horny layer. However, it can also have a type of "deep drying-out" effect on the living cell layers of the skin. The extent of surface drying can be determined, for example, using corneometry. The extent of deep drying (the reduction in deep moisture), by contrast, can be ascertained, for example, by cell size and/or cell volume determinations of living cells in the deeper skin layers, in particular the living cells of the epidermis.

Recent findings on the effect of UV-A rays on the skin have led to increased attention now being paid to the protective measures for this ray range. Virtually no sunscreen product manages without effective UV-A filter action anymore, pure UV-B filter preparations are rare.

The UV-A content of UV light also contributes to skin tanning: immediately after exposure to UV-A light, immediate pigment darkening (IPD) arises, although this also disappears again very quickly, offers no natural UV protection and additionally represents a rather undesired grayish tan. In addition, UV-A radiation also brings about a longer-lasting tan (permanent pigment darkening, PPD) which, on account of its properties, belongs between the delayed tanning DT and the immediate tanning IPD (with significant tendencies to IPD).

A number of compounds are also known for protecting against UV-A radiation, such as, in particular, dibenzoylmethane derivatives. Further known UV-A filter substances are certain water-soluble, sulfonated UV filter substances, such as, for example phenylene-1,4-bis(2-benzimidazyl)-3, 3'-5,5'-tetrasulfonic acid and its salts.

A healthy (natural) tan is viewed by the consumer as being desirable. Of importance here is not only a general "somehow darker" complexion, but rather a sporty, vital and fresh (natural) skin tanning, as is gained by gradual (gentle) sunbathing which does not lead to sunburn. The skin tanning which arises, for example, after a sunbed session is, by contrast, regarded as being unnatural or grayish. The color tone which can be achieved with self-tanning compositions as sole pigmentation carriers also barely corresponds to the color of natural healthy skin.

When applying a sunscreen composition to the skin, the ultraviolet rays can be attenuated by two effects: firstly by reflection and scattering of the rays at the surface of pulverulent solids (physical photoprotection) and secondly by absorption on chemical substances (chemical photoprotection). Depending on which wavelength range is absorbed, a distinction is made here between UV-B filters (absorption range 280 to 320 nm), UV-A filters (absorption range 320 to 400 nm) and broadband filters (absorption range 290 to about 380 nm). The group of broadband filters includes, for example, asymmetrically substituted s-triazine compounds, such as, for example, 2,4-bis{[4-(2-ethylhexyloxy)-2-hydroxylphenyl}-6-(4-methoxyphenyl)-1,3,5-triazine (INCI: Bis-Ethylhexyloxy]phenol Methoxyphenyl Triazine), certain benzophenones, such as, for example, 2-hydroxy-4-methoxybenzophenone (INCI: Benzophenone-3) or 2,2'-methylenebis(6-(2H-benzotriazol-2-yl)-4-(1,1,3,3-tetramethylbutyl)phenol) (INCI: Methylene Bis-Benzotriazolyl Tetramethylenebutylphenol).

The use concentration of known photoprotective filter substances is currently usually determined by the composition of the cosmetic or dermatological photoprotective preparation.

Accordingly, the aim of developing photoprotective products of the prior art is to achieve higher sun protection factors and/or UV-A protection performance and, in a simple and cost-effective manner, to arrive at preparations which, with the lowest possible concentrations of conventional UV filter substances, nevertheless achieve an acceptable or even high UV-A and/or UV-B protection performance. The color tone of the skin which can be achieved after use and exposure has hitherto, by contrast, played no role in developing a sunscreen product.

SUMMARY OF THE INVENTION

The object of the present invention was therefore, in a simple manner, to arrive at photoprotective preparations which are characterized in that the color tone obtained with their help is as close as possible to the natural skin color tone, the aim at the same time being to protect and increase the vitality and also the moisture of the skin. It was a further object of the invention to find preparations which increase the endogenous protection against UV radiation.

It was surprising and unforeseeable to the person skilled in the art that cosmetic or dermatological preparations which have a UVA balance of more than 15 would overcome the disadvantages of the prior art.

For the purposes of the present invention, particular preference is given to photoprotective preparations which have a UVA balance of more than 15.

The preparations according to the present invention are entirely satisfactory preparations in every regard and are not restricted to a limited choice of raw materials. Accordingly, they are quite particularly suitable for being used as a base for preparation forms with diverse application purposes. The preparations according to the present invention exhibit very good sensory and cosmetic properties, such as, for example, the distributability on the skin or the absorption capacity into the skin, and are further characterized by a very good photoprotection effectiveness, an exceptionally high UV-A and UV-B protection performance, and by excellent resistance to water, perspiration, sand and rubbing.

The preparations within the meaning of the present invention also surprisingly increase and improve the cellular vitality of the skin cells (which can also be referred to as "cell performance" or homeostasis of cell physiology etc.) and the "cellular firming" (in particular improvement and stabilization of the cytoskeleton) of the skin. Moreover, they also lead to an energy depot being started or enlarged in the cells which can rapidly provide available energy. This can take place, for example, through the endogenous cellular creatine system (ATP/creatine-ADP/creatine phosphate system).

It has also been found that the formulations according to the invention protect against sunburn particularly well.

In addition, they also improve the endogenous UV protection system, in particular the endogenous UV-A protection system, and also protect the immune system of the skin. In this way, the use of preparations according to the invention permits on the one hand an immediate (acute) protection in direct temporal relation to their use and, moreover, an (endogenous) protection which builds up over prolonged exposure to the sun and use of the preparations, which forms, for example, during the first days of a "sun holiday" and becomes better and better as it develops. By using preparations within the meaning of the present invention, the risk of UV-induced and/or photoinduced allergies (such as, for example sun allergy, polymorphous photodermatosis etc.) is also reduced, meaning that the preparations are exceptionally suitable for use with photosensitive skin. It has been found that the entire immune system of the skin and of the body is protected and even improved.

The use of preparations according to the invention also increases the skin moisture and the deep moisture of the skin, this skin-moistening care effect and protection against moisture loss lasting for several hours or even over the whole day or even longer.

When using the preparations according to the invention it has also been found that, besides an improved deep moisture, they bring about special protection (deep protection) of the deeper layers of skin (the living epidermis and in particular the dermis).

In addition, the preparations according to the present invention protect skin cells and skin against premature aging and optically perceptible changes and aid the skin in its regeneration and repair of damage which can occur in particular as a result of the effect of UV radiation.

It was also surprising that the preparations according to the invention are particularly suitable for preventing and reducing wrinkles and lines, and that they lead to a smoothing of the skin. It has also been found that use of the preparations according to the invention leads to a refining and reduction of the pores and thus to a more even skin image.

It was also surprising that the preparations within the meaning of the present invention protect the skin effectively from the harmful effects of UV exposure immediately after or during their application, whereas the preparations of the prior art usually have to be applied some time before sunbathing in order to be able to develop optimum protection.

The UVA balance, also called UV balance, is defined as:

$$UVA\ \text{Balance} = \frac{PPD_{in\ vitro} - 1}{SPF_{in\ vivo} - 1} \cdot 100$$

and is described in detail in DIN 67502. The PPD value is usually determined in vitro, for example as described by Wendel et al. (Wendel V. et al., 2003, The influence of pre-irradiation on the predictability of in vivo UVA protection with a new in vitro method, *Photodermatol Photoimmunol Photomed*, 19:93-97). Alternatively, the PPD value can also be determined in vivo. The value of the SPF (Sun Protection Factor, also called LPF for Light Protection Factor) is determined in vivo in accordance with COLIPA.

The UVA balance describes the ratio between the UVB protection performance and the UVA protection performance of a product. This ratio is usually determined by the formula specified above in accordance with DIN 67502. However, this ratio can also be expressed with the help of other parameters and methods. In particular, these may be methods analogous to the above DIN in which the products are irradiated prior to the actual in vitro measurement with sunlight or fractions of sunlight, in particular with UV light.

Formulations according to the invention are characterized by a balanced UVA and UVB protection in the sense of complete UV protection against natural sunlight.

DETAILED DESCRIPTION OF THE PREFERRED EMBODIMENTS

Particularly advantageous preparations within the meaning of the present invention have a UVA balance of more than 22, in particular more than 30, very particularly preferably more than 40.

It was also surprising that the use of preparations according to the invention permits both a targeted tanning behavior in the sense of natural tanning, and also the increase in the endogenous protection (i.e. the typical skin absorption behavior brought about by sun-simulated UV light/sunlight).

It was particularly surprising that preparations with the same light protection factor (LPF) also exhibit different effects depending on the level of the UV-A balance, although, (at an identical LPF) the UV-B fraction which reaches the skin is of course comparable. The UV-B fraction of light is responsible for skin erythema (sunburn), which is used to determine the LPF. Accordingly, it would have been expected that, for the same UV-B protection, further effects induced by UV-B radiation in the skin (with regard to natural tanning and endogenous protection) are also comparable. Instead, it is, however, surprisingly found that as the UVA balance increases firstly the tanning becomes more natural (and indeed: the higher the UVA balance, the more natural the color tone achieved during tanning) and secondly the endogenous UV protection which builds up in the skin is increased. The higher the UVA balance, the higher the endogenous absorption in the UV range, i.e. in a wavelength range between 300 and 390 nm.

Within the meaning of the present invention, "natural color tone" and "naturalness of the skin color tone" are understood as meaning that the tan obtained using the photoprotective preparations according to the invention through subsequent exposure to UV light and/or sunlight is comparable with the skin tan or the skin color tone which is achieved by gentle suntanning. Whether a skin color tone should be referred to as natural can be determined, for example, by ascertaining the Natural Tanning Factor (NTF).

To describe a natural tan and to determine the Natural Tanning Factor (NTF), reflectance spectra of the skin are recorded using a standard commercial spectrometer by means of light guides. They are recorded on an untanned area of skin (for example on the pale inside of the arm) and on a tanned area of skin (for example on the suntanned outer arm). The spectrum for the tanned area of skin (e.g. the outer arm) is divided in terms of wavelength by the spectrum for the untanned area of skin (e.g. the inside of the arm), i.e. standardized.

The reflectance spectrum for the "untanned area of skin" can alternatively be recorded, for example, also before treatment (for example with UV filter-containing formulations and subsequent irradiation) of a certain area. This area is then treated and measured again when treatment is complete, which may extend over several days. In this case, the second measurement corresponds to the above-described reflectance spectrum of the tanned area of skin.

If product treatment takes place which may also be combined with an irradiation, standardization with regard to the starting state of the area under investigation may prove particularly useful. In some cases, it is also very particularly useful if the spectra are standardized both with regard to the untreated state and also with regard to the starting state (double standardization).

For further evaluation, the standardized, or the double-standardized, spectrum is used in each case.

Comparing then the standardized spectra for the untreated skin tanned naturally and gently (i.e. avoiding sunburn and the like) with those which have been recorded following multiple application of the photoprotective preparation according to the invention and in each case subsequent exposure to UV light and/or sunlight, the more alike the shape and progress of the curves, the more natural the tan can be said to be.

The NTF describes the characteristic course of an individual standardized spectrum. It corresponds to the ratio of the difference (as a measure of the increase in the spectra in these ranges) of the reflection values at 410 nm ($R_{410}$) and at 500 nm ($R_{500}$) to the difference in the reflection values at 620 nm ($R_{620}$) and 750 nm ($R_{750}$):

$$NTF=(R_{410}-R_{500})/(R_{620}-R_{750}).$$

For natural tanning within the meaning of the present invention, the NTF is between 1.5 and 5. It is particularly advantageous if the NTF is between 1.5 and 3.5, preferably between 2.5 and 3.5 and especially preferably between 2.8 and 3.2.

Whether a natural tan is produced with the help of a photoprotective preparation can thus be ascertained by means of a statistical test in which the individual NTFs of gently suntanned skin are compared with those of the skin tanned following application of the photoprotective preparation of the same group of subjects or a different one. If there is no statistically relevant difference between the two sets of data, the tans are said to be equal and, accordingly, the artificial tan can be regarded as natural.

It will be appreciated that such a test can also be evaluated by purely visible means—for example by the subjects themselves—or with the help of another measurement method with which color impressions can be determined.

Besides the visible effects discussed ("natural color tone" and "naturalness of the skin color tone") which—as shown above—can be described with the help of the NTF, there is, moreover, also the endogenous skin protection against UV light which is brought about through the use of the formulations according to the invention with subsequent exposure to UV light or sunlight.

Within the meaning of the present invention, "natural endogenous skin protection" against UV light is understood as meaning that the endogenous skin protection obtained using the photoprotective preparations with subsequent exposure to UV light and/or sunlight is comparable with the endogenous or skin's own natural protection which is achieved through gentle suntanning. The performance of the endogenous skin protection can be determined, for example, by ascertaining the Endogenous Protection Factor (EPF) and the "independent Endogenous Protection Factor" ($EPF_{ind.}$). While the EPF is influenced by the degree of tanning of the skin, the $EPF_{ind.}$ is "independent" of the degree of tanning of the skin.

The EPF and the $EPF_{ind.}$ can also be ascertained from the reflectance spectra already described.

This is because if the standardized spectra for the untreated, naturally and gently tanned skin (i.e. avoiding sunburn and the like) are compared with those which have been recorded following multiple application of the photoprotective preparation according to the invention and in each case subsequent exposure to UV light and/or sunlight, then the more similar the shape and progress of the curves in the wavelength range 290 to 400 nm, the better the natural endogenous protection can be said to be. This effect can be made more independent of the tanning depth if the last-mentioned spectra are standardized to the intensity at 700 nm.

The EPF is thus a measure of the endogenous protective effect and is calculated from the standardized spectra in accordance with the following formula:

$$EPF = \frac{\int_{310}^{400} R\, d\lambda \text{ untreated}}{\int_{310}^{400} R\, d\lambda \text{ treated}}$$

The $EPF_{ind}$ is a factor which is largely independent of the visible depth of tanning. It gives the ratio of the endogenous protective effect in the UV region to the protective effect in the visible region (VIS region) of a standardized spectrum and is calculated according to the following formula:

$$EPF_{ind} = \frac{\left(9000 - \int_{310}^{400} R\, d\lambda \text{ treated}\right) * 380}{\left(38000 - \int_{400}^{780} R\, d\lambda \text{ treated}\right) * 90}$$

In this formula, the 380 corresponds to the length of the wavelength interval 400 nm to 780 nm and 90 to the length of the wavelength interval 310 nm to 400 nm. The values 9000 and 38 000 correspond here to 100%×90 and 100%×380 respectively and give the integral size for the unprotected skin. Since R is likewise given in %, the percentage sign in the formula can be dispensed with.

$EPF_{ind}$ values greater than 1 indicate that the UV protection for the area of skin under consideration is greater than the VIS protection.

It is particularly advantageous within the meaning of the present invention if the $EPF_{ind}$ is greater than 1.5, preferably greater than 2, particularly preferably greater than 2.5 and very particularly preferably greater than 3.

One way of describing the endogenous protection is the calculation of the minimum of the abovementioned spectra: the more displaced the local minimum with regard to the wavelength in the direction of UVB, the more effective the protection against UVB radiation compared to longer-wave radiation. It is particularly advantageous within the meaning of the present invention if the minimum is at a wavelength less than 390 nm, preferably less than 370 nm, particularly preferably less than 350 nm and very preferably less than 330 nm.

The statistical evaluation of the EPF and of the $EPF_{ind}$ is carried out analogously to the NTF.

Since the effects which are described by NTF, EPF and $EPF_{ind}$ are long-lasting endogenous effects over days and weeks, the formulations according to the invention lead to a long-lasting (UV) protection and/or to long-lasting natural tanning. These effects last at least 2 days, generally more than 5 days beyond the last application of the preparations according to the invention.

The UVA balance according to the invention can be achieved by combining customary UV filter substances. The UV filter substances are advantageously chosen from one or more of the following groups: UV-A, UV-B and/or broadband filter substances, and organic and inorganic pigments as UV filter substances.

Advantageous UV filter substances within the meaning of the present invention are:
dibenzoylmethane derivatives, in particular 4-(tert-butyl)-4'-methoxydibenzoylmethane (CAS No. 70356-09-1), which is sold by Givaudan under the name Parsole 1789 and by Merck under the trade name Eusolex® 9020.
phenylene-1,4-bis(2-benzimidazyl)-3,3'-5,5'-tetrasulfonic acid and its salts, particularly the corresponding sodium, potassium or triethanolammonium salts, in particular phenylene-1,4-bis(2-benzimidazyl)-3,3'-5,5'-tetrasulfonic acid bis-sodium salt with the INCI name Disodium Phenyl Dibenzimidazole Tetrasulfonate (CAS No. 180898-37-7), which is available, for example, under the trade name Neo Heliopan AP from Symrise;
salts of 2-phenylbenzimidazole-5-sulfonic acid, such as its sodium, potassium or its triethanolammonium salt, and the sulfonic acid itself with the INCI name Phenylbenzimidazole Sulfonic Acid (CAS No. 27503-81-7), which is available, for example, under the trade name Eusolex 232 from Merck or under Neo Heliopan Hydro from Symrise;
1,4-di(2-oxo-10-sulfo-3-bornylidenemethyl)benzene (also: 3,3'-(1,4-phenylenedimethylene)bis(7,7-dimethyl-2-oxobicyclo[2.2.1]hept-1-ylmethanesulfonic acid or benzene-1,4-di(2-oxo-3-bornylidenemethyl-10-sulfonic acid) with the INCI name Terephthalidene Dicamphor Sulfonic Acid (CAS No.: 90457-82-2) and salts thereof, particularly the corresponding 10-sulfato compounds, in particular the corresponding sodium, potassium or triethanolammonium salt and is available, for example, under the trade name Mexoryl SX from Chimex;
sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and salts thereof.
benzoxazole derivatives, such as, for example, 2,4-bis[5-1 (dimethylpropyl)benzoxazol-2-yl(4-phenyl)imino]-6-(2-ethylhexyl)imino-1,3,5-triazine with the CAS No. 288254-16-0, which is available from 3V Sigma under the trade name Uvasorb® K2A.
hydroxybenzophenones, e.g. hexyl 2-(4'-diethylamino-2'-hydoxybenzoyl)benzoate (also: aminobenzophenone), which is available under the trade name Uvinul A Plus from BASF.
triazine derivatives, such as, for example, 2,4-bis{[4-(2-ethylhexyloxy)-2-hydroxy]phenyl}-6-(4-methoxyphenyl)-1,3,5-triazine (INCI: Bis-Ethylhexyloxylphenol Methoxyphenyl Triazine), which is available under the trade name Tinosorb® S from CIBA-Chemikalien GmbH; dioctylbutylamidotriazone (INCI: Diethylhexyl Butamido Triazone), which is available under the trade name UVASORB HEB from Sigma 3V; tris(2-ethylhexyl) 4,4',4''-(1,3,5-triazine-2,4,6-triyltriimino)tris-benzoate, also: 2,4,6-tris[anilino(p-carbo-2'-ethyl-1'-hexyloxy)]-1,3,5-triazine (INCI: Ethylhexyl Triazone), which is sold by BASF Aktiengesellschaft under the trade name Uvinul® T 150, and 2-[4,6-bis(2,4-di methylphenyl)-1,3,5-triazin-2-yl]-5-(octyloxy)phenol (CAS No.: 2725-22-6).
benzotriazoles, such as, for example, 2,2'-methylenebis(6-(2H-benzotriazol-2-yl)-4-(1,1,3,3-tetramethylbutyl) phenol) with the INCI name Methylene Bis-Benztriazolyl Tetramethylbutylphenol, which is available, for example, under the trade name Tinosorb® M from CIBA-Chemikalien GmbH.
3-benzylidenecamphor derivatives, preferably 3-(4-methylbenzylidene)camphor, 3-benzylidenecamphor;
4-aminobenzoic acid derivatives, preferably 2-ethylhexyl 4-(dimethylamino)benzoate, amyl 4-(dimethylamino) benzoate;
esters of benzalmalonic acid, preferably di(2-ethylhexyl) 4-methoxybenzalmalonate;
esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

2-(2H-benzotriazol-2-yl)-4-methyl-6-(2-methyl-3-(1,3,3,3-tetramethyl-1-(trimethylsilyloxy)disiloxanyl)propyl) phenol (INCI: Drometrizole Trisiloxane), which is available under the trade name Mexoryl XL from Chimex and UV filters bonded to polymers ethylhexyl 2-cyano-3,3-diphenylacrylate (INCI: Octocrylene), which is available from BASF under the name Uvinul® N 539 T.

To achieve a high UV-A protection and a so-called "box-shaped" absorption spectrum, the use of certain UVA and/or broadband filter substances, such as, for example, 1,4-di(2-oxo-10-sulfo-3-bornylidenemethyl)benzene and its salts (e.g. Terephthalylidene Dicamphor Sulfonic Acid (INCI)) and Drometrizole Trisiloxane (INCI) may be useful. It was surprising and unforseeable to the person skilled in the art, however, that, within the meaning of the present invention, the formulations in which the mentioned UV filter substances Terephthalylidene Dicamphor Sulfonic Acid and Drometrizole Trisiloxane are not present are particularly advantageous.

Within the meaning of the present invention it is particularly advantageous, instead of the UV filter substances Terephthalylidene Dicamphor Sulfonic Acid and Drometrizole Trisiloxane, to use organic UVA filter substances in amounts which are matched to the light protection factor of the formulations. This means that the ratio of the amounts of UV-A filter used to the amounts of UV-B filter used must be sufficiently high.

Preferred mixing ratios of UVA filters to UVB filters are in the range from 0.1 to 4 (based on the masses of the UV filters used). Particularly preferred mixing ratios of UVA filters to UVB filters are in the range from 0.2 to 2.5 (based on the masses of the UV filters used). Very particularly preferred mixing ratios of UVA filters to UVB filters are in the range from 0.3 to 1 (based on the masses of the UV filters used). The group of UVA filters preferred according to the invention includes, inter alia, the above-described dibenzoylmethane derivatives, 1,4-di(2-oxo-10-sulfo-3-bornylidenemethyl) benzene and salts thereof and in particular phenylene-1,4-bis (2-benzimidazyl)-3,3'-5,5'-tetrasulfonic acid and its salts, 2,4-bis[5-1 (dimethylpropyl)benzoxazol-2-yl(4-phenyl) imino]-6-(2-ethylhexyl)imino-1,3,5-triazine or hexyl 2-(4'-diethylamino-2'-hydroxybenzoyl)benzoate (also: aminobenzophenone). The group of UV-B filters preferred according to the invention includes, inter alia, the above-described salts of 2-phenylbenzimidazole-5-sulfonic acid, dioctylbutylamidotriazone, ethylhexyltriazone, 3-benzylidenecamphor derivatives, esters of cinnamic acid, octocrylenes and UV-B filters bonded to polymers.

Further particularly advantageous preparations within the meaning of the present invention which are characterized by a high or very high UVA balance preferably comprise so-called organic broadband filters in concentrations of 0.5% by weight (based on the total weight of the preparation) and above. The group of broadband filters includes, for example, asymmetrically substituted s-triazine compounds, such as, for example, 2,4-bis{[4-(2-ethylhexyloxy)-2-hydroxy]phenyl}-6-(4-methoxyphenyl)-1,3,5-triazine, certain benzophenones, such as, for example, 2-hydroxy-4-methoxybenzophenone or 2,2'-methylenebis(6-(2H-benzotriazol-2-yl)-4-(1,1,3,3-tetramethylbutyl)-phenol). The use of pigmentary, inorganic UV filters in concentrations of 0.5% by weight or more is also advantageous. This group includes, in particular, metal oxides, such as titanium dioxide and zinc oxide, which offer both protection against UVB and also UVA radiation. Within the meaning of the present invention, formulations which comprise as UV filter substances exclusively broadband filters or broadband filters in combination with pigmentary inorganic UV filters are likewise advantageous. Broadband filters preferred according to the invention are benzotriazoles and triazine derivatives, particular preference being given to 2,4-bis{[4-(2-ethylhexyloxy)-2-hydroxy]phenyl}-6-(4-methoxyphenyl)-1,3,5-triazine).

Advantageous preparations according to the invention have a sun protection factor of at least 5, preferably at least 10, more preferably at least 20 and very particularly preferably at least 30, the sun protection factor being determined in accordance with the COLIPA method.

In addition to one or more UV filter substances, particularly advantageous preparations within the meaning of the present invention also comprise substances which start or enlarge cellular energy depots. Active ingredients suitable for this purpose are, for example, creatine/creatinine (e.g. in the ratios 100:1, preferably 50:1 to 3:1, particularly preferably in the ratio 3:1) and taurine.

Cosmetic or dermatological preparations within the meaning of the present invention comprise—based on the total weight of the preparations—advantageously 0.001 to 10% by weight, in particular 0.01 to 5% by weight and very particularly 0.1 to 2% by weight, of creatine/creatinine, taurine or mixture thereof.

The skin is positively influenced under the protection of the UV filters and through the positive properties of the applied active ingredients creatine and/or taurine, especially with regard to its vitality, and overall is also protected against the undesired effects of premature skin aging and acute sunburn.

The invention therefore also provides the use of cosmetic or dermatological photoprotective preparations with a UVA balance of more than 15 and a content of creatine/creatinine, taurine or mixture thereof for improving and/or increasing the vitality and the endogenous protection of skin cells and for protecting the skin against optically perceptible changes.

The cosmetic or dermatological preparations according to the invention can have the customary composition and serve for the treatment, care of the skin and as make-up product in decorative cosmetics. The cosmetic and dermatological preparations according to the invention can also advantageously be in the form of a product for the care of the hair and/or of the scalp, in particular a product for arranging the hair which is used while blow-drying the hair or a styling and treatment product.

For use, the preparations according to the invention are applied to the skin or the hair in a sufficient amount in the manner customary for cosmetics.

Besides one or more oil phases, the preparations within the meaning of the present invention can additionally preferably comprise one or more water phases and be, for example, in the form of O/W, W/O/W or O/W/O emulsions. Such formulations can preferably also be solids emulsions (i.e. emulsions which are stabilized by solids, e.g. Pickering emulsions), gel emulsions (gel emulsions or gel creams are sensorially particularly light products with a low content of emulsifiers, structurants or builders (e.g. fatty alcohols) and lipids), hydrodispersions and also gels.

Advantageous preparations within the meaning of the present invention are emulsions, in particular micropigment emulsions and O/W and W/O emulsions. Also advantageous within the meaning of the present invention are spray formulations.

O/W Emulsions

O/W emulsions within the meaning of the present invention advantageously comprise one or more emulsifiers chosen from the group: polyglyceryl-2 dipolyhydroxystearate, glyceryl stearate citrate, glyceryl stearate, polyglyceryl-3 methylglucose distearate, stearic acid, PEG-40 stearate, sodium cetearyl sulfate, hydrogenated cocoglycerides, and one or more coemulsifiers, such as, for example, fatty alcohols, in particular cetearyl alcohol and/or stearyl alcohol.

The oil phase of O/W emulsions according to the invention advantageously comprises oil components chosen from the group: butylene glycol dicaprylate/dicaprate, dicaprylyl ether, $C_{12-15}$-alkyl benzoate, $C_{18-38}$-fatty acid triglyceride, dibutyl adipate, cyclomethicone.

W/O Emulsions

W/O emulsions within the meaning of the present invention advantageously comprise one or more emulsifiers chosen from the group: polyglyceryl-2 dipolyhydroxystearate, PEG-30 dipolyhydroxystearate.

The oil phase of W/O emulsions according to the invention advantageously comprises oil components chosen from the group: butylene glycol dicaprylate/dicaprate, paraffinum liquidum, $C_{12-15}$-alkyl benzoate, $C_{18-38}$-fatty acid triglyceride, isopropyl stearate, cetyldimethicone.

Sprayable Emulsions, in Particular Microemulsions

Sprayable O/W emulsions, in particular O/W microemulsions are also particularly advantageous within the meaning of the present invention.

The droplet diameters of the customary "simple", i.e. non-multiple, emulsions are in the range from about 1 μm to about 50 μm. Such "macroemulsions" are, without further coloring additives, milky-white in color and opaque. Finer "macroemulsions" whose droplet diameters are in the range from about 0.5 μm to about 1 μm are, again without coloring additives, bluish-white in color and opaque. Such "macroemulsions" usually have a high viscosity.

The droplet diameter of microemulsions within the meaning of the present invention, by contrast, is in the range from about 50 to about 500 nm. Such micoemulsions are bluish-white in color to translucent and mostly of low viscosity. The viscosity of many microemulsions of the O/W type is comparable with that of water.

An advantage of microemulsions is that, in the dispersed phase, active ingredients can be present in substantially more finely dispersed form than in the dispersed phase of "macroemulsions". A further advantage is that they are sprayable on account of their low viscosity. If microemulsions are used as cosmetics, corresponding products are characterized by high cosmetic elegance.

Of advantage according to the invention are, in particular, O/W microemulsions which are obtainable with the help of so-called phase-inversion temperature technology and comprise at least one emulsifier (emulsifier A) which is chosen from the group of emulsifiers whose lipophilicity is dependent on the temperature. Their lipophilicity increases by increasing the temperature and decreases by lowering the temperature.

Advantageous emulsifiers A are, for example, polyethoxylated fatty acids (PEG-100 stearate, PEG-20 stearate, PEG-150 laureth, PEG-8 distearate and the like) and polyethoxylated fatty alcohols (ceteareth-12, ceteareth-20, isoceteth-20, beheneth-20, laureth-9 etc.) and alkyl polyglycosides (cetearyl glycoside, stearyl glycoside, palmityl glycoside etc.).

If the phase inversion is triggered essentially by varying the temperature, O/W emulsions, in particular O/W microemulsions, are obtainable where the size of the oil droplets is determined essentially by the concentration of the emulsifier or the emulsifiers used, in such a way that a higher emulsifier concentration results in relatively small droplets, and a lower emulsifier concentration results in relatively large droplets. The droplet sizes are generally between 20 and 500 nm.

Within the meaning of the present invention, it is in some instances advantageous to use further W/O and/or O/W emulsifiers which do not fall under the definition of emulsifier A, for example in order to increase the water resistance of the preparations according to the present invention. For example, alkylmethicone copolyols and alkyldimethicone copolyols (in particular cetyldimethicone copolyol, laurylmethicone copolyol), W/O emulsifiers (such as, for example, sorbitan stearate, glyceryl stearate, glycerol stearate, sorbitan oleate, lecithin, glyceryl isostearate, polyglyceryl-3 oleate, polyglyceryl-3 diisostearate, PEG-7 hydrogenated castor oil, polyglyceryl-4 isostearate, acrylate/$C_{10-30}$-alkyl acrylate crosspolymer, sorbitan isostearate, poloxamer 101, polyglyceryl-2 dipolyhydroxystearate, polyglyceryl-3 diisostearate, polyglyceryl-4 dipolyhydroxystearate, PEG-30 dipolyhydroxystearate, diisostearoyl polyglyceryl-3 diisostearate, glycol distearate and polyglyceryl-3 dipolyhydroxystearate), and fatty acid esters of sulfuric acid or phosphoric acid (cetyl phosphate, trilaureth-4 phosphate, trioleth-8 phosphate, stearyl phosphate, cetearyl sulfate etc.) can be used.

Further advantageous sprayable O/W emulsions within the meaning of the present invention are low-viscosity cosmetic or dermatological hydrodispersions which comprise at least one oil phase and at least one water phase, where the preparation is stabilized by at least one gel former and does not necessarily have to comprise emulsifiers, but may comprise one or more emulsifiers.

Advantageous gel formers for such preparations are, for example, copolymers of $C_{10-30}$-alkyl acrylates and one or more monomers of acrylic acid, of methacrylic acid or esters thereof. The INCI name of such compounds is "Acrylates/C 10-30 Alkyl Acrylate Crosspolymer". The Pemulen® grades TR 1, TR 2 and TRZ from Goodrich (Noveon) are particularly advantageous.

Carbopols are also advantageous gel formers for such preparations. Carbopols are polymers of acrylic acid, in particular also acrylate-alkyl acrylate copolymers. Advantageous carbopols are, for example, the grades 907, 910, 934, 940, 941, 951, 954, 980, 981, 1342, 1382, 2984 and 5984, likewise the ETD grades 2020, 2050 and Carbopol Ultrez 10. Further advantageous gel formers for such preparations are xanthan gum, cellulose derivatives and carob seed flour.

Possible (optional) emulsifiers which may be used are ethoxylated fatty alcohols or ethoxylated fatty acids (in particular PEG-100 stearate, ceteareth-20) and/or other nonionic surface-active substances.

In addition, the very low-viscosity to sprayable emulsions may also advantageously be W/O emulsions or water-in-silicone oil (W/S) emulsions. W/O and W/S emulsions which comprise
- at least one silicone emulsifier (W/S) with an HLB value of <8, at least one W/O emulsifier with an HLB value of <7 or mixtures thereof and
- optionally an O/W emulsifier with an HLB value of >10 are particularly advantageous.

Such preparations further comprise at least 20% by weight of lipids, where the lipid phase can also advantageously comprise silicone oils, or even consist entirely of such oils.

The silicone emulsifier or emulsifiers can advantageously be chosen from the group of alkylmethicone copolyols and/or alkyldimethicone copolyols (e.g. dimethicone copolyols which are sold by Goldschmidt AG under the trade names ABIL® B 8842, ABIL® B 8843, ABIL® B 8847, ABIL® B 8851, ABIL® B 8852, ABIL® B 8863, ABIL® B 8873 and ABIL® B 88183, cetyldimethicone copolyol [Goldschmidt AG/ABIL® EM 90], cyclomethiconedimethicone copolyol [Goldschmidt AG/ABIL® EM 97], laurylmethicone copolyol [Dow Corning Ltd./Dow Corning® 5200 formulation aid], octyldimethicone ethoxyglucoside [Wacker].

The W/O emulsifier or emulsifiers with an HLB value of <7 can advantageously be chosen from the following group: sorbitan stearate, sorbitan oleate, lecithin, glyceryl lanolate, lanolin, hydrogenated castor oil, glyceryl isostearate, polyglyceryl-3 oleate, pentaerythrithyl isostearate, methylglucose dioleate, methylglucose dioleate in a mixture with hydroxystearate and beeswax, PEG-7 hydrogenated castor oil, polyglyceryl-4 isostearate, hexyl laurate, acrylate/$C_{1-30}$-alkyl acrylate crosspolymer, sorbitan isostearate, polyglyceryl-2 dipolyhydroxystearate, polyglyceryl-3 diisostearate, PEG-30 dipolyhydroxystearate, diisostearoylpolyglyceryl-3-diisostearate, polyglyceryl-3 dipolyhydroxystearate, polyglyceryl-4-dipolyhydroxystearate, polyglyceryl-3 dioleate.

The O/W emulsifier or emulsifiers with an HLB value of >10 can advantageously be chosen from the following group: glyceryl stearate in a mixture with ceteareth-20, ceteareth-25, ceteareth-6 in a mixture with stearyl alcohol, cetylstearyl alcohol in a mixture with PEG-40 castor oil and sodium cetylstearyl sulfate, triceteareth-4 phosphate, glyceryl stearate, sodium cetylstearyl sulfate, lecithin trilaureth-4 phosphate, laureth-4 phosphate, stearic acid, propylene glycol stearate SE, PEG-9 stearate, PEG-20 stearate, PEG-30 stearate, PEG-40 stearate, PEG-100 stearate, ceteth-2, ceteth-20, polysorbate-20, polysorbate-60, polysorbate-65, polysorbate-100, glyceryl stearate in a mixture with PEG-100 stearate, ceteareth-3, isostearyl glyceryl ether, cetylstearyl alcohol in a mixture with sodium cetylstearyl sulfate, PEG-40 stearate, glycol distearate, polyglyceryl-2 PEG-4 stearate, ceteareth-12, ceteareth-20, ceteareth-30, methylglucose sesquistearate, steareth-10, PEG-20 stearate, steareth-21, steareth-20, isosteareth-20, PEG-45/dodecyl glycol copolymer, glyceryl stearate SE, ceteth-20, PEG-20 methylglucose sesquistearate, glyceryl stearate citrate, cetyl phosphate, cetearyl sulfate, sorbitan sesquioleate, triceteareth-4 phosphate, trilaureth-4 phosphate, polyglyceryl methylglucose distearate, potassium cetyl phosphate, isosteareth-10, polyglyceryl-2 sesquiisostearate, ceteth-10, isoceteth-20, glyceryl stearate in a mixture with ceteareth-20, ceteareth-12, cetylstearyl alcohol and cetyl palmitate, PEG-30 stearate, PEG-40 stearate, PEG-100 stearate.

Aqueous-alcoholic solutions are also advantageous. They can comprise from 0% by weight to 90% by weight of ethanol. Aqueous-alcoholic solutions within the meaning of the present invention can advantageously also comprise solubility promoters, such as, for example, PEG-40 or PEG-60 hydrogenated castor oil.

The preparations according to the present invention can advantageously also be used as cosmetic or dermatological impregnation solutions with which water-insoluble substrates in particular—such as, for example, woven or non-woven wipes—are moistened. Impregnation solutions of this type are preferably of low viscosity, in particular sprayable (such as, for example, PIT emulsions, hydrodispersions, W/O emulsions, oils, aqueous solutions etc.) and preferably have a viscosity of less than 2000 mPa·s, in particular less than 1500 mPa·s (measuring device: Haake viscotester VT-02 at 25° C.).

They can be used to obtain, for example, cosmetic sunscreen wipes, care wipes and the like, which represent the combination of a soft, water-insoluble material with the low-viscosity cosmetic and dermatological impregnation solution.

Foams

Also particularly advantageous within the meaning of the present invention are self-foaming, foam-like, after-foaming or foamable cosmetic and dermatological preparations.

"Self-foaming", "foam-like", "after-foaming" and "foamable" preparations are understood as meaning preparations from which foams can in principle be produced by introducing one or more gases—whether during the preparation process, whether upon use by the consumer or in another way. In such foams, the gas bubbles are (randomly) distributed in one (or more) liquid phase(s), where the (foamed) preparations do not necessarily have to have the appearance of a foam in macroscopic terms. (Foamed) cosmetic or dermatological preparations according to the invention (referred to below for the sake of simplicity also as foams) may, for example, be macroscopically visibly dispersed systems of gases dispersed in liquids. The foam character may, however, for example also only be visible under a (light) microscope. Moreover, foams according to the invention—particularly when the gas bubbles are too small to be seen under a light microscope—are also evident from the considerable volume increase of the system.

Within the meaning of the present invention, such preparations advantageously comprise an emulsifier system which consists of A. at least one emulsifier A chosen from the group of completely neutralized, partially neutralized or unneutralized branched and/or unbranched, saturated and/or unsaturated fatty acids with a chain length of from 10 to 40 carbon atoms, B. at least one emulsifier B chosen from the group of polyethoxylated fatty acid esters with a chain length of from 10 to 40 carbon atoms and with a degree of ethoxylation of from 5 to 100 and C. at least one coemulsifier C chosen from the group of saturated and unsaturated, branched and unbranched fatty alcohols with a chain length of from 10 to 40 carbon atoms.

The emulsifier or the emulsifiers A are preferably chosen from the group of fatty acids, which are completely or partially neutralized with customary alkalis (such as, for example, sodium hydroxide and potassium hydroxide, sodium carbonate and potassium carbonate, and mono- and triethanolamine). Stearic acid and stearates, isostearic acid and isostearates, palmitic acid and palmitates, and myristic acid and myristates, for example, are particularly advantageous.

The emulsifier or the emulsifiers B are preferably chosen from the following group: PEG-9 stearate, PEG-8 distearate, PEG-20 stearate, PEG-8 stearate, PEG-8 oleate, PEG-25 glyceryl trioleate, PEG-40 sorbitan lanolate, PEG-15 glyceryl ricinoleate, PEG-20 glyceryl stearate, PEG-20 glyceryl isostearate, PEG-20 glyceryl oleate, PEG-20 stearate, PEG-20 methylglucose sesquistearate, PEG-30 glyceryl isostearate, PEG-20 glyceryl laurate, PEG-30 stearate, PEG-30 glyceryl stearate, PEG-40 stearate, PEG-30 glyceryl laurate, PEG-50 stearate, PEG-100 stearate and PEG-150 laurate. Polyethoxylated stearic esters, for example, are particularly advantageous.

According to the invention, the coemulsifier or the coemulsifiers C are preferably chosen from the following group: behenyl alcohol ($C_{22}H_{45}OH$), cetearyl alcohol [a mixture of cetyl alcohol ($C_{16}H_{33}OH$) and stearyl alcohol ($C_{18}H_{37}OH$)], lanolin alcohols (wool wax alcohols which are the unsaponifiable alcohol fraction of wool wax which is obtained following saponification of wool wax). Cetyl and cetylstearyl alcohol are particularly preferred.

It is advantageous according to the invention to choose the weight ratios of emulsifier A to emulsifier B to coemulsifer C (A:B:C) as a:b:c, where a, b and c, independently of one another, may be rational numbers from 1 to 5, preferably from 1 to 3. A weight ratio of, for example, 1:1:1 is particularly preferred.

It is advantageous within the meaning of the present invention to choose the total amount of the emulsifiers A and B and of the coemulsifier C from the range from 2 to 20% by weight, advantageously from 5 to 15% by weight, in particular from 7 to 13% by weight, in each case based on the total weight of the formulation.

Pickering/Solids-Stabilized Emulsions

Also particularly advantageous within the meaning of the present invention are cosmetic or dermatological preparations which have been stabilized only by very finely divided solids particles. Such "emulsifier-free" emulsions are also referred to as Pickering emulsions.

In Pickering emulsions, the solid material accumulates at the oil/water interface in the form of a layer, as a result of which coalescence of the dispersed phases is prevented. Of essential importance here are, in particular, the surface properties of the solids particles, which should exhibit both hydrophilic and also lipophilic properties.

The stabilizing solids particles can also advantageously be treated ("coated") on the surface to repel water, the aim being to form or retain an amphiphilic character of these solids particles. The surface treatment can consist in providing the solids particles with a thin hydrophobic or hydrophilic layer by methods known per se.

The average particle diameter of the microfine solids particles used as stabilizer is preferably chosen to be less than 100 μm, particularly advantageously less than 50 μm. In this connection, it is essentially unimportant in what form (platelets, rods, spheres, etc.) or modification the solids particles used are present.

The microfine solids particles are preferably chosen from the group of amphiphilic metal oxide pigments. Of particular advantage are:
- titanium dioxides (coated and uncoated): e.g. Eusolex T-2000 from Merck, titanium dioxide MT-100 Z from Tayca Corporation
- zinc oxides, e.g. Z-Cote and Z-Cote HP1 from BASF AG, MZ-300, MZ-500 and MZ-505M from Tayca Corporation
- iron oxides.

Furthermore, it is advantageous if the microfine solids particles are chosen from the following groups: boron nitrides, starch derivatives (tapioca starch, sodium corn starch octynyl succinate etc.), talc, latex particles.

It is advantageous according to the invention if the solids-stabilized emulsions comprise significantly less than 0.5% by weight of one or more emulsifiers or are even entirely emulsifier-free.

The cosmetic and dermatological preparations according to the invention can comprise cosmetic auxiliaries as are customarily used in such preparations, e.g. preservatives, preservative aids, complexing agents, bactericides, perfumes, substances for preventing or increasing foaming, pigments which have a coloring effect, thickeners, moisturizing and/or humectant substances, fillers which improve the feel on the skin, fats, oils, waxes and other customary constituents of a cosmetic or dermatological formulation, such as alcohols, polyols, polymers, foam stabilizers, electrolytes, organic solvents or silicone derivatives.

Advantageous preservatives within the meaning of the present invention are, for example, formaldehyde donors (such as, for example, DMDM hydantoin, which is available, for example, under the trade name Glydant™ from Lonza), iodopropyl butylcarbamates (e.g. those available under the trade names Glycacil-L, Glycacil-S from Lonza, and/or Dekaben LMB from Jan Dekker), parabens (i.e. alkyl p-hydroxybenzoates, such as methyl-, ethyl-, propyl- and/or butylparaben), phenoxyethanol, ethanol, benzoic acid and the like. In addition, the preservative system according to the invention also usually advantageously comprises preservative aids, such as, for example, octoxyglycerol, glycine soya etc.

Advantageous complexing agents within the meaning of the present invention are, for example, EDTA, [S,S]-ethylenediamine disuccinate (EDDS), which is available, for example, under the trade name Octaquest from Octel, pentasodium ethylenediamine tetramethylenephosphonate, which is available, for example, under the trade name Dequest 2046 from Monsanto and/or iminodisuccinic acid, which is available, inter alia, from Bayer AG under the trade names Iminodisuccinate VP OC 370 (about 30% strength solution) and Baypure CX 100 solid.

Particularly advantageous preparations are also obtained if antioxidants are used as additives or active ingredients. According to the invention, the preparations advantageously comprise one or more antioxidants. Favorable, but nevertheless optional, antioxidants which may be used are all antioxidants customary or suitable for cosmetic and dermatological applications.

Within the meaning of the present invention, water-soluble antioxidants may be used particularly advantageously, such as, for example, vitamins, e.g. ascorbic acid and derivatives thereof—in particular ascorbyl palmitate, Na and Mg ascorbyl phosphate and ascorbyl acetate—and rutinic acid and derivatives thereof, in particular alpha-glucosylrutin, quercetin and isoquercetin.

Particularly preferred antioxidants are also vitamin E and derivatives thereof (in particular vitamin E acetate), vitamin A and derivatives thereof (in particular vitamin A palmitate) and carnosine, lipoic acid and its derivatives (in particular dihydrolipoic acid and liponamide), butylhydroxytoluene, butylhydroxyanisole, beta-alanine and carotenoids (in particular beta-carotene) and phytoene.

The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and/or derivatives thereof are the antioxidant or the antioxidants, it is advantageous to choose their respective concentrations from the range from 0.001 to 10% by weight, based on the total weight of the formulation.

If vitamin A or vitamin A derivatives, or carotenes or derivatives thereof are the antioxidant or the antioxidants, it is advantageous to choose their respective concentrations from the range from 0.001 to 10% by weight, based on the total weight of the formulation.

It is particularly advantageous if the cosmetic preparations according to the present invention comprise cosmetic or dermatological active ingredients, preferred active ingredients being antioxidants which can protect the skin against oxidative stress.

Further active ingredients to be used advantageously within the meaning of the present invention are those which have a positive influence on the condition of the skin, such as, in particular, active ingredients for positively influencing aging skin which reduce the development of lines or else existing lines. Of particular advantage are bioquinones, in particular ubiquinone (Q10), ubiquinol, folic acid and its derivatives (in particular tetrahydrofolic acid and dihydrofolic acid), niacin and its derivatives (in particular niacinamide), creatine and creatinine, carnitine, biotin, isoflavone, cardiolipin, lipoic acid, antifreezing proteins, hop and hop-malt extracts. Agents which promote the restructuring of connective tissue, such as isoflavonoids and isoflavonoid-containing plant extracts—such as, for example, soya and clover extracts—can also be used very readily in the formulations according to the invention. It is also found that the formulations are particularly suitable for using active ingredients for aiding the skin functions in dry skin (such as, for example, vitamin C, biotin, carnitine, propionic acid, green tea extracts, eucalyptus oil, urea and mineral salts (such as, for example, NaCl, sea minerals), and osmolytes (such as, for example, inositol, betaine, quaternary ammonium compounds)). In a similar way, the incorporation of active ingredients for alleviating or positively influencing irritative skin conditions, whether for sensitive skin in general or for skin irritated by noxae (UV light, chemicals) has proven to be advantageous. Mention is made here of active ingredients such as sericosides, various extracts of licorice, licochalcones, in particular licochalcone A, silymarin, silyphos, dexpanthenol, inhibitors of prostaglandin metabolism, in particular of cyclooxygenase and of leukotriene metabolism, in particular of 5-lipoxygenase, but also of the 5-lipoxygenase inhibitor protein, FLAP. The abovementioned active ingredients are also particularly suitable for starting or replacing an (energy) depot, and for activating the repair of various cellular structures, in particular DNA. The incorporation of pigmentation modulators has also proven to be advantageous. Mention is made here of active ingredients which reduce the pigmentation of the skin and thus lead to a cosmetically desired lightening of the skin, reduce the appearance of age spots or lighten existing age spots. By way of example, mention may be made of tyrosine sulfate, dioic acid (8-hexadecene-1,16-dicarboxylic acid), and lipoic acid and liponamide, various extracts of licorice, kojic acid, hydroquinone, arbutin, alpha-arbutin, deoxyarbutin, fruit acids, in particular alpha-hydroxy acids (AHAs), bearberry (Uvae ursi), ursolic acid, ascorbic acid, green tea extracts, aminoguanidine, pyridoxamine, niacinamide, inhibitors of Proteinase Activated Receptor 2 (PAR-2). Particular preference is also given to formulations according to the invention which comprise further active ingredients which bring about an increased or more rapid tanning of the skin, be it with or without the effect of UV light. Examples of such active ingredients which can be used are Advanced Glycation Endproducts (AGE), lipofuscins, nucleic acid oligonucleotides, purines and pyrimidines, NO-releasing substances, tyrosine and its derivatives (in particular N-acetyl tyrosine), phenylalanine and its derivatives, in particular N-acetylphenylalanine, and activators of Proteinase Activated Receptors 2 (PAR-2).

Formulations according to the invention which comprise, for example, known antiwrinkle active ingredients, such as flavone glycosides (in particular α-glycosylrutin), coenzyme Q10, vitamin E and its derivatives and the like are particularly advantageously suitable for the prophylaxis and treatment of cosmetic or dermatological changes in the skin, as arise, for example, during skin aging (such as, for example, dryness, roughness and formation of dryness wrinkles, itching, reduced regreasing (e.g. after washing), visible vascular dilations (telangiectasias, couperosis), flaccidity and formation of lines and wrinkles, local hyperpigmentation, hypopigmentation and incorrect pigmentation (e.g. age spots), increased susceptibility to mechanical stress (e.g. cracking) and the like). In addition, they are advantageously suitable for countering the appearance of dry or rough skin.

It is also advantageous to use the active ingredient or the active ingredients in encapsulated form, e.g. in collagen matrices and other customary encapsulation materials, such as, for example, cyclic oligosaccharides (in particular alpha-, beta-, HP-beta-, random-Me-beta-, gamma-cyclodextrin), alpha-, beta- or gamma-cyclodextrins being used as encapsulation materials to correspond to the chemical properties of the compounds according to the invention known to the person skilled in the art. In addition, it may be advantageous to use the active ingredients or mixtures thereof in the form of cellulose encapsulations, in gelatin, wax matrices or liposomally encapsulated.

In the case of encapsulation with cyclodextrins, it is assumed that the cyclodextrin backbones act as host molecule and the active ingredient according to the invention as guest molecule. For the preparation, cyclodextrins are dissolved in water and active ingredient is added thereto. The molecular adduct then precipitates out as a solid and can be subjected to the customary purification and work-up steps. It is known that cyclodextrin guest complexes in a corresponding solvent (e.g. water) are in an equilibrium between the concrete guest-cyclodextrin complex and the dissociated form, it being possible for cyclodextrin and guest to be separated to a certain extent. Such equilibrium systems are likewise advantageous within the meaning of the present invention.

The water phase of the preparations according to the present invention can advantageously comprise customary cosmetic auxiliaries, such as, for example, alcohols, in particular those of low carbon number, preferably ethanol and isopropanol, polymers, foam stabilizers, electrolytes, and in particular one or more thickeners, which may advantageously be chosen from the group consisting of silicon dioxide, aluminum silicates, polysaccharides or derivatives thereof, e.g. hyaluronic acid, xanthan gum, hydroxypropylmethylcellulose, particularly advantageously from the group of polyacrylates, preferably a polyacrylate from the group of so-called carbopols [from Noveon], for example carbopol grades 980, 981, 1382, 2984, 5984, ETD 2020, ETD 2050, pemulen TR-1 or -2, Ultrez 10, in each case individually or in combination.

In addition, the preparations according to the present invention can advantageously also comprise self-tanning substances, such as, for example, dihydroxyacetone, melanin derivatives and erythrulose, these substances being used in concentrations of from 0.1% by weight to 8% by weight, based on the total weight of the preparation. In addition, besides dihydroxyacetone, the formulations according to the invention can also advantageously comprise nut extracts and further substances which reportedly maintain or produce or additionally enhance the tan.

In addition, the preparations according to the present invention can advantageously also comprise repellents for protection against flies, ticks and spiders and the like. For example, N,N-diethyl-3-methylbenzamide (trade name: Meta-delphene, "DEET"), dimethyl phthalate (trade name: Palatinol M, DMP), and in particular ethyl 3-(N-n-butyl-N-acetylamino)propionate (available under the trade name Insekt Repellent® 3535 from Merck) are advantageous. The repellents can either be used individually or in combination.

Moisturizers is the term used to refer to substances or mixtures of substances which impart to cosmetic or dermatological preparations the property, following application or distribution on the surface of the skin, of reducing moisture release by the horny layer (also called trans-epidermal water loss (TEWL)) and/or of positively influencing hydration of the horny layer.

Within the meaning of the present invention, the moisturizer or the moisturizers are advantageously chosen from the group: glycerol, lactic acid and/or lactates, in particular sodium lactate, butylene glycol, propylene glycol, biosaccharide gum-1, glycine soya, ethylhexyloxyglycerol, pyrrolidonecarboxylic acid and urea. In addition, it is particularly advantageous to use polymeric moisturizers from the group of water-soluble, water-swellable or water-gellable polysaccharides. Hyaluronic acid, chitosan and a fucose-rich polysaccharide, which is filed in the Chemical Abstracts under the Registry number 178463-23-5 and which is available, for example, under the name Fucogel®1000 from SOLABIA S.A., for example, are particularly advantageous. Moisturizers can advantageously also be used as antiwrinkle active ingredients for the prophylaxis and treatment of cosmetic or dermatological changes in the skin, as arise, for example, during skin aging. It is particularly advantageous within the meaning of the present invention to use glycerol as moisturizer, preferably in a concentration of from 0.05 to 30% by weight, particularly preferably 1 to 10% by weight, in each case based on the total weight of the preparation.

The cosmetic or dermatological preparations according to the invention can also advantageously, but not necessarily, comprise fillers which, for example, further improve the sensory and cosmetic properties of the formulations and, for example, bring about or enhance a velvety or silky feel on the skin. Advantageous fillers within the meaning of the present invention are starch and starch derivatives (such as, for example, tapioca starch, distarch phosphate, aluminum or sodium starch octenylsuccinate and the like), pigments which have neither a primarily UV filter effect nor a coloring effect (such as, for example, boron nitride etc.) and Aerosils® (CAS No. 7631-86-9).

The oil phase of the formulations according to the invention is advantageously chosen from the group of polar oils, for example from the group of lecithins and fatty acid triglycerides, namely the triglycerol esters of saturated and unsaturated, branched and unbranched alkanecarboxylic acids of chain length from 8 to 24, in particular 12 to 18, carbon atoms. The fatty acid triglycerides can, for example, be chosen advantageously from the group of synthetic, semisynthetic and natural oils, such as, for example, cocoglyceride, olive oil, sunflower oil, soya oil, peanut oil, rapeseed oil, almond oil, palm oil, coconut oil, castor oil, wheatgerm oil, grapeseed oil, thistle oil, evening primrose oil, macadamia nut oil and the like.

Also advantageous according to the invention are, for example, natural waxes of animal and vegetable origin, such as, for example, beeswax and other insect waxes, and berry wax, shea butter and lanolin (wool wax).

Further advantageous polar oil components may, within the meaning of the present invention, also be chosen from the group of esters of saturated and unsaturated, branched and unbranched alkanecarboxylic acids of chain length from 3 to 30 carbon atoms and saturated and unsaturated, branched and unbranched alcohols of chain length from 3 to 30 carbon atoms, and from the group of esters of aromatic carboxylic acids and saturated and unsaturated, branched and unbranched alcohols of chain length from 3 to 30 carbon atoms. Such ester oils can then advantageously be chosen from the group consisting of octyl palmitate, octyl cocoate, octyl isostearate, octyidodecyl myristate, octyidodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as, for example, jojoba oil.

In addition, the oil phase can advantageously be chosen from the group of dialkyl ethers and dialkyl carbonates, advantageous examples being dicaprylyl ether (Cetiol OE) and/or dicaprylyl carbonate, for example that available under the trade name Cetiol CC from Cognis.

It is also preferred to choose the oil component or the oil components from the group consisting of isoeicosane, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethyl isosorbide. It is particularly advantageous if the oil phase of the formulations according to the invention has a content of $C_{12-15}$-alkyl benzoate or consists entirely of this.

Advantageous oil components are also, for example, butyloctyl salicylate (for example that available under the trade name Hallbrite BHB from CP Hall), hexadecyl benzoate and butyloctyl benzoate and mixtures thereof (Hallstar AB) and/or diethylhexyl naphthalate (Hallbrite TQ or Corapan TQ from Symrise).

Any mixtures of such oil and wax components can also be used advantageously within the meaning of the present invention.

Furthermore, the oil phase can likewise advantageously also comprise nonpolar oils, for example those which are chosen from the group of branched and unbranched hydrocarbons and hydrocarbon waxes, in particular mineral oil, Vaseline (petrolatum), paraffin oil, squalane and squalene, polyolefins, hydrogenated polyisobutenes and isohexadecane. Among the polyolefins, polydecenes are the preferred substances.

In addition, the oil phase can advantageously have a content of cyclic or linear silicone oils or consist entirely of such oils, although it is preferred to use an additional content of other oil phase components apart from the silicone oil or the silicone oils.

Silicone oils are high molecular weight synthetic polymeric compounds in which silicon atoms are joined via oxygen atoms in a chain-like or reticular manner and the remaining valences of the silicon are saturated by hydrocarbon radicals (in most cases methyl groups, more rarely ethyl, propyl, phenyl groups etc.). Systematically, the silicone oils are referred to as polyorganosiloxanes. The methyl-substituted polyorganosiloxanes, which represent the most significant compounds of this group in terms of amount and are characterized by the following structural formula

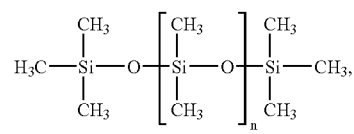

are also referred to as polydimethylsiloxane or dimethicone (INCI). Dimethicones come in various chain lengths and with various molecular weights.

Particularly advantageous polyorganosiloxanes within the meaning of the present invention are, for example, dimethylpolysiloxanes [poly(dimethylsiloxane)], which are available, for example, under the trade names Abil 10 to 10 000 from Th. Goldschmidt.

Also advantageous are phenylmethylpolysiloxanes (INCI: Phenyl Dimethicone, Phenyl Trimethicone), cyclic silicones (octamethylcyclotetrasiloxane and decamethylcyclopentasiloxane), which are also referred to as Cyclomethicones in accordance with INCI, amino-modified silicones (INCI: Amodimethicones) and silicone waxes, e.g. polysiloxanepolyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Th. Goldschmidt. Other silicone oils can, however, also be used advantageously within the meaning of the present invention, for example cetyldimethicone, hexamethylcyclotrisiloxane, polydimethylsiloxane, poly(methylphenylsiloxane).

The examples below are intended to illustrate the present invention without limiting it. The numerical values in the examples are percentages by weight, based on the total weight of the particular preparations.

EXAMPLES

O/W Emulsions: High Protection, SPF 20

| INCI | 1 | 2 | 3 | 4 | 5 | 6 | 7 | 8 | 9 |
|---|---|---|---|---|---|---|---|---|---|
| Alcohol Denat. | 3 | 4 | 2 | 0 | 3 | 5 | 5 | 5 | 5 |
| Acrylates/C10–30 Alkyl Acrylate Crosspolymer | 0.1 | 0.05 | 0.2 | 0.05 | 0 | 0 | 0 | 0 | 0 |
| Polyglyceryl-2 Dipolyhydroxystearate | 0.25 | 0.5 | 0.6 | 0.5 | 0 | 0 | 0 | 0 | 0 |
| Glyceryl Stearate Citrate | 1 | 2 | 3 | 2.5 | 0 | 0 | 0 | 0 | 0 |
| Glyceryl Stearate SE | 0 | 0 | 0 | 0 | 2 | 1 | 1 | 1 | 1 |
| Cetearyl Alcohol + PEG-40 Castor Oil + Sodium Cetearyl Sulfate | 0 | 0 | 0 | 0 | 5 | 2.5 | 2.5 | 2.5 | 2.5 |
| VP/Hexadecene Copolymer | 0.5 | 0.5 | 0.4 | 0.5 | 0.2 | 0.5 | 0.5 | 0.5 | 0.5 |
| Trisodium EDTA | 1 | 0.5 | 1 | 1 | 1 | 1 | 1 | 1 | 1 |
| Preservatives | q.s. | q.s. | q.s. | q.s. | q.s. | q.s. | q.s. | q.s. | q.s. |
| Terephthalidene Dicamphor Sulfonic Acid | | | | | | | 5 | 10 | 10 |
| Drometrizole Trisiloxane | | | | | | | 5 | 5 | 5 |
| Bis-Ethylhexyloxyphenol Methoxyphenyl Triazine | 0.5 | 1.4 | 1 | 2 | 0.5 | 1.4 | | | |
| Disodium Phenyl Dibenzimidazole Tetrasulfonate | | 1 | | 1.5 | | | | | |
| Ethylhexyl Triazone | 1 | 1.6 | 3.5 | 4 | 0 | 0 | 0 | 0 | 0 |
| Butyl Methoxydibenzoylmethane | 4.5 | 3.5 | 3.5 | 3 | 4.5 | 4.5 | 4.5 | 4.8 | 4.8 |
| Ethylhexyl Methoxycinnamate | 8 | 8 | 0 | 0 | 6 | 5 | | | |
| 2,4-Bis[5-1(dimethylpropyl)benzoxazol-2-yl-(4-phenyl)imino]-6-(2-ethylhexyl)imino-1,3,5-triazine | | 1.5 | | | | | | 5 | 3 |
| Aminobenzophenone | 1 | | | | | | | 4 | 8 |
| Octocrylene | 0 | 0 | 0 | 0 | 2 | 3 | 10 | 10 | 10 |
| Phenylbenzimidazole Sulfonic Acid | 0 | 0 | 0 | 0 | 2 | 2 | | | |
| Ethylhexylglycerol | 0.5 | 0.5 | 0.5 | 0.5 | 0.5 | 0.5 | 0.5 | 0.5 | 0.5 |
| Glycerol | 5 | 7.5 | 7.5 | 6 | 2 | 8 | 8 | 8 | 8 |
| Hydrogenated Coco-Glycerides | 1 | 0 | 1 | 1 | 1 | 1 | 1 | 1 | 1 |
| Butylene Glycol Dicaprylate/Dicaprate | 3 | 2 | 9 | 8 | 4 | 2 | 2 | 2 | 2 |
| Dicaprylyl Ether | 2 | 3 | 1 | 4 | 1 | 2 | 2 | 2 | 2 |
| C12–15 Alkyl Benzoate | 5 | 8 | 7.5 | 6 | 8 | 4 | 4 | 4 | 4 |
| Dibutyl Adipate | 0 | 0 | 3 | 0 | 2 | 1 | 1 | 1 | 1 |
| Dihydroxyacetone (DHA) | 5 | | | 2 | | | 1 | | |
| Perfume | q.s. | q.s. | q.s. | q.s. | q.s. | q.s. | q.s. | q.s. | q.s. |
| Titanium Dioxide + Trimethoxycaprylylsilane | 3 | 3 | 3 | 3 | 3 | 3 | 5 | 5 | 5 |
| Cyclomethicone | 0 | 2 | 1 | 2 | 3 | 0 | 0 | 0 | 0 |
| Xanthan Gum | 0.2 | 0.1 | 0.4 | 0.2 | 0.4 | 0.25 | 0.25 | 0.25 | 0.25 |
| Stearyl Alcohol | 1 | 1.5 | 2 | 1.2 | 1 | 1.5 | 1.5 | 1.5 | 1.5 |
| Aqua | ad 100 | ad 100 | ad 100 | ad 100 | ad 100 | ad 100 | ad 100 | ad 100 | ad 100 |
| Creatinine | 0.05 | 0.1 | 0.03 | 0.05 | 0.06 | 0.05 | 0.05 | 0.05 | 0.05 |
| Dihydroxyacetone | | 3 | 5 | | | | | | |
| Tocopheryl Acetate | 0.5 | 0.2 | 0.5 | 0.5 | 0.5 | 0.5 | 0.5 | 0.5 | 0.5 |
| Creatine | 0.5 | 1 | 0.3 | 0.5 | 0.6 | 0.5 | 0.5 | 0.5 | 0.5 |
| Ascorbic Acid | | | | | | | 1.0 | 4.0 | 0.5 |
| Sodium Ascorbyl Phosphate | | | | | | 0.8 | 0.2 | | |

O/W Emulsions: Face Care

| INCI | 1 | 2 | 3 | 4 | 5 | 6 | 7 | 8 | 9 |
|---|---|---|---|---|---|---|---|---|---|
| Alcohol Denat. | | 3 | | 2 | | | 1 | 4 | 4 |
| Acrylates/C10–30 Alkyl Acrylate Crosspolymer | 0.1 | | | 0.1 | | 0.2 | | | |
| Glyceryl Stearate Citrate | 2.0 | 1.5 | 1.5 | | | | | | |
| Polyglyceryl-3 Methylglucose Distearate | | | | 2 | 4 | | | | |

-continued

| INCI | 1 | 2 | 3 | 4 | 5 | 6 | 7 | 8 | 9 |
|---|---|---|---|---|---|---|---|---|---|
| Sorbitan Stearate | | | | 1 | | | | | |
| Glyceryl Stearate SE | | | | | | | | 3 | |
| Glyceryl Stearate | | | | | | 1.5 | 1 | | |
| Stearic Acid | | | | | | 3 | 2.5 | 1.5 | 3 |
| PEG 40 Stearate | | | | | | | | | 1 |
| VP/Hexadecene Copolymer | | | 0.2 | | | 0.5 | | | |
| Trisodium EDTA | 1 | 1 | 1 | 1 | 1 | 1 | 1 | 1 | 1 |
| Preservatives | q.s. | q.s. | q.s. | q.s. | q.s. | q.s. | q.s. | q.s. | q.s. |
| Bis-Ethylhexyloxyphenol Methoxyphenyl Triazine | | | 1 | | | | | 1.5 | |
| Ethylhexyl Triazone | | | | | | 2 | 2 | | |
| Butyl Methoxydibenzoylmethane | 3 | 3 | | 4 | 2 | 3 | 4 | | 2 |
| Ethylhexyl Methoxycinnamate | 4 | 4 | 3 | | 5 | | 2 | | 5 |
| Octocrylene | | | | 5 | | | | | |
| Phenylbenzimidazole Sulfonic Acid | | | | 2 | | | | 2 | |
| Ethylhexylglycerol | 0.5 | | | | | | 0.5 | | |
| Glycerol | 7.5 | 10 | 7.5 | 10 | 10 | 10 | 7.5 | 7.5 | 7.5 |
| Hydrogenated Coco-Glycerides | 1.5 | | 1 | | | | 2 | | |
| Butylene Glycol Dicaprylate/Dicaprate | | 2 | | | | | | 2 | |
| Dicaprylyl Ether | 3 | 2 | | 3 | | | | 3 | |
| C12–15 Alkyl Benzoate | | 2 | | 1 | 4 | | | 2 | 2 |
| Myristyl Myristate | 1 | | | | | | 2 | | |
| Dicaprylyl Carbonate | | | 3 | | | | 1 | | 2 |
| Perfume | q.s. | q.s. | q.s. | q.s. | q.s. | q.s. | q.s. | q.s. | q.s. |
| Titanium Dioxide + Trimethoxycaprylylsilane | | | | 1 | | 1 | 0.5 | | |
| Cyclomethicone | 4 | 3 | | | | | 3 | | |
| Xanthan Gum | | 0.4 | | 0.4 | | | | | |
| Tapioca Starch | 3 | 1 | 2 | | | | | | 4 |
| Distarch Phosphate | | | | | 1 | | | 2 | |
| Stearyl Alcohol | 1 | 2 | | | | 2 | | 1 | 1 |
| Cetyl Alcohol | | 2 | | | | 2 | | | |
| Aqua | ad 100 | ad 100 | ad 100 | ad 100 | ad 100 | Ad 100 | ad 100 | ad 100 | ad 100 |
| Creatinine | 0.1 | 0.1 | | | 0.1 | 0.1 | | 0.1 | 0.1 |
| Taurine | | | 1.0 | 1.0 | 1.0 | | 1.0 | | |
| Tocopheryl Acetate | 0.5 | 0.5 | 0.5 | 0.5 | 0.5 | 0.5 | 0.5 | 0.5 | 0.5 |
| Creatine | 0.5 | 0.5 | | | 0.5 | 0.5 | 05 | 0.5 | 0.5 |
| Alpha-Glucosylrutin + Isoquercitrin | | 0.05 | | | | | | | |
| *Glycyrrhiza Inflata* Root Extract | 0.025 | | 0.025 | | | | | | |
| Ubiquinone | | | | 0.25 | | | | | |
| *Simmondsia Chinensis* (Jojoba) Seed Oil | | | | | 1 | | | | |
| Dioic Acid | | | | | | | 0.1 | 1 | 1 |

Sunsprays: High Protection, SPF 20

| INCI | 1 | 2 | 3 | 4 | 5 | 6 | 7 | 8 |
|---|---|---|---|---|---|---|---|---|
| Alcohol Denat. | 2 | 4 | 0 | 5 | 3.5 | 5 | 3.5 | 5 |
| Ceteareth-20 | 1 | 1 | 1 | 1 | 1 | 1 | 1 | 1 |
| VP/Hexadecene Copolymer | 0.5 | 0.5 | 0.5 | 0.5 | 0.5 | 0.5 | 0.5 | 0.5 |
| Trisodium EDTA | 1 | 1 | 1 | 1 | 1 | 1 | 1 | 1 |
| Preservatives | q.s. | q.s. | q.s. | q.s. | q.s. | q.s. | q.s. | q.s. |
| Bis-Ethylhexyloxyphenol Methoxyphenyl Triazine | 0.5 | 1 | 1 | 1.5 | | 1.5 | | 1.5 |
| Disodium Phenyl Dibenzimidazole Tetrasulfonate | | | 1 | | | 1 | | |
| Phenylbenzimidazole Sulfonic Acid | 2 | 1.5 | 2 | 2 | | 2 | | 2 |
| Ethylhexyl Triazone | 3 | 0 | 3 | 0 | 3 | 0 | 3 | 0 |
| Butyl Methoxydibenzoylmethane | 3.8 | 3.5 | 4.0 | 4.5 | 4.5 | 4.8 | | |
| Ethylhexyl Methoxycinnamate | 0 | 9 | 0 | 0 | | 0 | | 0 |
| 2,4-Bis[5-1(dimethylpropyl)benzoxazol-2-yl-(4-phenyl)imino]-6-(2-ethylhexyl)imino-1,3,5-triazine | 1 | | | | | | 8.8 | 9 |
| Hexyl 2-(4'-diethylamino-2'-hydroxybenzoyl)-benzoate | | 2 | | | | | 5.9 | 6.8 |
| Octocrylene | 0 | 0 | 0 | 3 | 10 | 10 | 10 | 10 |
| Ethylhexyl Salicylate | 0 | 0 | 0 | 4 | | 4 | | 4 |
| Terephthalidene Dicamphor Sulfonic Acid | | | | | 6 | 8.5 | 6 | 8.5 |
| Drometrizole Trisiloxane | | | | | 10 | 12 | 10 | 12 |
| Titanium Dioxide | | | | | 4 | 5 | 4 | 5 |
| Glycerol | 7.5 | 5 | 8 | 6 | 8 | 6 | 8 | 6 |
| C12–15 Alkyl Benzoate | 4 | 0 | 5 | 0 | 5 | 0 | 5 | 0 |
| Butylene Glycol Dicaprylate/Dicaprate | 8 | 4 | 7.5 | 3 | 7.5 | 3 | 7.5 | 3 |
| Perfume | q.s. | q.s. | q.s. | q.s. | q.s. | q.s. | q.s. | q.s. |
| Acrylates/C10–30 Alkyl Acrylate Crosspolymer | 0.2 | 0.4 | 0.3 | 0.5 | 0.3 | 0.5 | 0.3 | 0.5 |

-continued

| INCI | 1 | 2 | 3 | 4 | 5 | 6 | 7 | 8 |
|---|---|---|---|---|---|---|---|---|
| C18–36 Acid Triglyceride | 0.5 | 1 | 0.3 | 1 | 0.3 | 1 | 0.3 | 1 |
| Aqua | ad 100 | ad 100 | ad 100 | ad 100 | ad 100 | ad 100 | ad 100 | ad 100 |
| Creatinine | 0.06 | 0.05 | 0.05 | 0 | 0.05 | 0 | 0.05 | 0 |
| Dihydroxyacetone | | 4 | | | | | | |
| Tocopheryl Acetate | 0.5 | 0.5 | 0.5 | 0.5 | 0.5 | 0.5 | 0.5 | 0.5 |
| Creatine | 0.6 | 0.5 | 0.5 | 0 | 0.5 | 0 | 0.5 | 0 |
| Taurine | | | 0.1 | 0.3 | | 0.1 | | |

W/O Emulsions: High Protection, SPF 20

| INCI | 1 | 2 | 3 | 4 | 5 | 6 |
|---|---|---|---|---|---|---|
| Alcohol Denat. | 1 | 2 | 1 | 2 | 1 | 2 |
| Polyglyceryl-2 Dipolyhydroxystearate | 4 | 5.5 | 4 | 5.5 | 4 | 5.5 |
| Trisodium EDTA | 1 | 1 | 1 | 1 | 1 | 1 |
| Preservatives | q.s. | q.s. | q.s. | q.s. | q.s. | q.s. |
| Paraffinum Liquidum | 0 | 1.8 | 0 | 1.8 | 0 | 1.8 |
| Ethylhexyl Triazone | | | 1 | | | |
| Diethylhexyl Butamido Triazone | 0.5 | 0 | | | | |
| Bis-Ethylhexyloxyphenol Methoxyphenyl Triazine | 1 | 1 | | | | |
| 2,4-Bis[5-1(dimethylpropyl)benzoxazol-2-yl-(4-phenyl)imino]-6-(2-ethylhexyl)imino-1,3,5-triazine | | | 0.5 | | 9 | 8 |
| Aminobenzophenone | | | 0.5 | 0.8 | 6.4 | 5.5 |
| Octocrylene | 2.5 | 6 | 10 | 10 | 10 | 10 |
| Terephthalidene Dicamphor Sulfonic Acid | | | | 8 | | 8 |
| Drometrizole Trisiloxane | | | 12 | | 12 | |
| Disodium Phenyl Dibenzimidazole Tetrasulfonate | | | 1 | | | |
| Butyl Methoxydibenzoylmethane | 3.5 | 0.9 | 4 | 4.7 | | |
| Ethylhexyl Methoxycinnamate | 7.5 | 0 | 7.5 | 0 | 7.5 | 0 |
| Ethylhexylglycerol | 0.5 | 0.5 | 0.5 | 0.5 | 0.5 | 0.5 |
| Butylene Glycol | 5 | 5 | 5 | 5 | 5 | 5 |
| Glycerol | 7.5 | 5 | 7.5 | 5 | 7.5 | 5 |
| Isopropyl Stearate | 3 | 6 | 3 | 6 | 3 | 6 |
| Butylene Glycol Dicaprylate/Dicaprate | 7.5 | 8 | 7.5 | 8 | 7.5 | 8 |
| C12–15 Alkyl Benzoate | 9.5 | 5 | 9.5 | 5 | 9.5 | 5 |
| Perfume | q.s. | q.s. | q.s. | q.s. | q.s. | q.s. |
| Sodium Starch Octenylsuccinate | 0.4 | 0.55 | 0.4 | 0.55 | 0.4 | 0.55 |
| Titanium Dioxide | 4.5 | 2.5 | 5 | 6 | 5 | 6 |
| Magnesium Sulfate | 0.3 | 0.2 | 0.3 | 0.2 | 0.3 | 0.2 |
| Cetyl Dimethicone | 0 | 0.5 | 0 | 0.5 | 0 | 0.5 |
| Glycine | 0.2 | 0.5 | 0.2 | 0.5 | 0.2 | 0.5 |
| C18–36 Acid Triglyceride | 0.5 | 1 | 0.5 | 1 | 0.5 | 1 |
| Aqua | ad 100 | ad 100 | ad 100 | ad 100 | ad 100 | ad 100 |
| Creatine | | 0.5 | | | | |
| Creatinine | | 0.05 | | | | |
| Taurine | 1 | | | | | |
| Tocopheryl Acetate | 0.5 | 0.5 | 0.5 | 0.5 | 0.5 | 0.5 |
| Panthenol | 0 | 0.75 | 0 | 0.75 | 0 | 0.75 |

W/O Emulsions: Very High or Ultra High Protection, SPF 30/40/50/50+

| INCI | 1 | 2 | 3 | 4 | 5 | 6 | 7 | 8 |
|---|---|---|---|---|---|---|---|---|
| Alcohol Denat. | 1 | 2 | 3 | 0 | 3 | 2 | 3 | 2 |
| Polyglyceryl-2 Dipolyhydroxystearate | 4 | 5.8 | 5 | 0 | 5 | 0 | 5 | 0 |
| PEG-30 Dipolyhydroxystearate | 0 | 0 | 0 | 3.5 | 0 | 3.5 | 0 | 3.5 |
| Trisodium EDTA | 1 | 1 | 1 | 1 | 1 | 1 | 1 | 1 |
| Preservative system | q.s. | q.s. | q.s. | q.s. | q.s. | q.s. | q.s. | q.s. |
| Diethylhexyl Butamido Triazone | 0.5 | | 1 | | 0 | 2 | 0 | 2 |
| Ethylhexyl Triazone | | 0.5 | | 2 | | | | |
| Bis-Ethylhexyloxyphenol Methoxyphenyl Triazine | 1 | 2 | 3 | 2.5 | 3 | 2.5 | 3 | 2.5 |
| 2,4-Bis[5-1(dimethylpropyl)benzoxazol-2-yl-(4-phenyl)imino]-6-(2-ethylhexyl)imino-1,3,5-triazine | | 1 | | | | | 5.9 | 9.4 |
| Hexyl 2-(4'-diethylamino-2'-hydoxybenzoyl)-benzoate | | | 0.5 | | | | 9.5 | 9.3 |
| Octocrylene | 2.5 | 3.5 | 2.5 | 3 | 10 | 3 | 10 | 3 |
| Terephthalidene Dicamphor Sulfonic Acid | | | | | 9.5 | | 9.5 | |

-continued

| INCI | 1 | 2 | 3 | 4 | 5 | 6 | 7 | 8 |
|---|---|---|---|---|---|---|---|---|
| Drometrizole Trisiloxane | | | | | 12 | | 12 | |
| Disodium Phenyl Dibenzimidazole Tetrasulfonate | 0.5 | | | | | | | 1 |
| Butyl Methoxydibenzoylmethane | 3.5 | 4.5 | 0.9 | 4 | 4.7 | 4 | 2 | |
| Ethylhexyl Methoxycinnamate | 7.5 | 7.5 | 0.5 | 0.5 | 0.5 | 0.5 | 0.5 | 0.5 |
| Ethylhexylglycerol | 0.5 | 0.5 | 0.5 | 0.5 | 0.5 | 0.5 | 0.5 | 0.5 |
| Butylene Glycol | 2.5 | 2.5 | 5 | 4 | 5 | 4 | 5 | 4 |
| Glycerol | 7.5 | 7.5 | 5 | 6 | 5 | 6 | 5 | 6 |
| Isopropyl Stearate | 4 | 2.5 | 8 | 5 | 8 | 5 | 8 | 5 |
| Butylene Glycol Dicaprylate/Dicaprate | 7 | 6.5 | 8 | 6 | 8 | 6 | 8 | 6 |
| C12–15 Alkyl Benzoate | 9 | 7 | 8 | 5 | 8 | 5 | 8 | 5 |
| Perfume | q.s. | q.s. | q.s. | q.s. | q.s. | q.s. | q.s. | q.s. |
| Titanium Dioxide | 4.5 | 5 | 4.5 | 6 | 10 | 6 | 10 | 6 |
| Magnesium Sulfate | 0.3 | 0.1 | 0.2 | 0.2 | 0.2 | 0.2 | 0.2 | 0.2 |
| Cetyl Dimethicone | 0 | 0.5 | 0 | 0.2 | 0 | 0.2 | 0 | 0.2 |
| Dihydroxyacetone | | | 5 | | | | | |
| Glycine | 0.3 | 0.4 | 0.5 | 0.5 | 0.5 | 0.5 | 0.5 | 0.5 |
| C18–36 Acid Triglyceride | 0.4 | 0.6 | 0.5 | 0.45 | 0.5 | 0.45 | 0.5 | 0.45 |
| Tocopheryl Acetate | 0.5 | 0.5 | 0.5 | 0.5 | 0.5 | 0.5 | 0.5 | 0.5 |
| Panthenol | 0 | 0 | 1.5 | 1.5 | 1.5 | 1.5 | 1.5 | 1.5 |
| Aqua | ad 100 | ad 100 | ad 100 | ad 100 | ad 100 | ad 100 | ad 100 | ad 100 |

Photoprotective Emulsions: Very High Protection SPF 30/40/50

| INCI | 1 | 2 | 3 | 4 | 5 | 6 |
|---|---|---|---|---|---|---|
| Alcohol Denat. | 3 | 3 | 0 | 3 | 0 | 0 |
| Glyceryl Stearate SE | 1.5 | 1 | 0 | 1 | 0 | 0 |
| PEG-30 Dipolyhydroxystearate | 1 | 0 | 0 | 0 | 0 | 0 |
| Cetearyl Alcohol + PEG-40 Castor Oil + Sodium Cetearyl Sulfate | 3.75 | 2.5 | 0 | 2.5 | 0 | 0 |
| Cetyl PEG/PPG-10/1 Dimethicone | 0 | 0.8 | 3.8 | 0.8 | 3.8 | 3.8 |
| Polyglyceryl-2 Dipolyhydroxystearate | 0 | 0 | 2 | 0 | 2 | 2 |
| Trisodium EDTA | 1 | 1 | 0 | 1 | 0 | 0 |
| Preservative system | q.s. | q.s. | q.s. | q.s. | q.s. | q.s. |
| Cera Microcristallina + Paraffinum Liquidum | 0 | 0 | 3 | 0 | 3 | 3 |
| 2,4-Bis[5-1(dimethylpropyl)benzoxazol-2-yl-(4-phenyl)imino]-6-(2-ethylhexyl)imino-1,3,5-triazine | | | | 8.9 | 8.1 | 8.9 |
| Hexyl 2-(4'-diethylamino-2'-hydoxybenzoyl)-benzoate | | | | 5.9 | 6.4 | 9 |
| Terephthalidene Dicamphor Sulfonic Acid | | | | | | 9.2 |
| Drometrizole Trisiloxane | | | | | | 13 |
| Glycerol | 7.5 | 3 | 5 | 3 | 5 | 5 |
| Butylene Glycol | 0 | 0 | 5 | 0 | 5 | 5 |
| Hydrogenated Coco-Glycerides | 0.5 | 0.5 | 0 | 0.5 | 0 | 0 |
| Dicaprylyl Carbonate | 1 | 2.35 | 0 | 2.35 | 0 | 0 |
| Caprylic/Capric Triglyceride | 5 | 4 | 7 | 4 | 7 | 7 |
| Butylene Glycol Dicaprylate/Dicaprate | 7.5 | 8 | 6 | 8 | 6 | 6 |
| C12–15 Alkyl Benzoate | 0 | 0 | 1.5 | 0 | 1.5 | 1.5 |
| Dicaprylyl Ether | 0 | 0 | 5 | 0 | 5 | 5 |
| Perfume | 0 | 0 | q.s. | 0 | q.s. | q.s. |
| Zinc Oxide + Dimethicone | 7 | 8 | 8 | 15 | 10 | 10 |
| Titanium Dioxide | 8 | 9 | 9 | 20 | 15 | 15 |
| Magnesium Sulfate | 0 | 0 | 0.3 | 0 | 0.3 | 0.3 |
| Cyclomethicone | 0 | 0 | 4 | 0 | 4 | 4 |
| Glycine | 0 | 0 | 0.5 | 0 | 0.5 | 0.5 |
| Xanthan Gum | 0.2 | 0.3 | 0 | 0.3 | 0 | 0 |
| C18–36 Acid Triglyceride | 0.5 | 1 | 0 | 1 | 0 | 0 |
| Cetyl Alcohol | 1 | 1.5 | 0 | 1.5 | 0 | 0 |
| Aqua | ad 100 | ad 100 | ad 100 | ad 100 | ad 100 | ad 100 |
| Tocopheryl Acetate | 0.5 | 0.5 | 0.5 | 0.5 | 0.5 | 0.5 |
| Dioic acid | 0.1 | | | | | |
| Panthenol | 0 | 0 | 1.4 | 0 | 1.4 | 1.4 |

O/W Emulsions: Ultra High Protection, SPF 50+

| INCI | 1 | 2 | 3 | 4 | 5 | 6 | 7 | 8 | 9 |
|---|---|---|---|---|---|---|---|---|---|
| Alcohol Denat. | 4 | | 2 | 4 | 4 | 0 | 3 | 4 | 4 |
| Glyceryl Stearate SE | 1 | 1.5 | 2 | 2 | 1.2 | 2 | 1.2 | 1.2 | 1.2 |

| INCI | 1 | 2 | 3 | 4 | 5 | 6 | 7 | 8 | 9 |
|---|---|---|---|---|---|---|---|---|---|
| Cetearyl Alcohol + PEG-40 Castor Oil + Sodium Cetearyl Sulfate | 2.5 | 3.75 | 5 | 5 | 2.9 | 5 | 2.9 | 2.9 | 2.9 |
| VP/Hexadecene Copolymer | 0.5 | 0.5 | 0.8 | 0.7 | 0 | 0.7 | 0.2 | 0.2 | 0.2 |
| Trisodium EDTA | 1 | 1 | 0 | 1 | 1.5 | 1 | 1 | 1 | 1 |
| Preservatives | q.s. | q.s. | q.s. | q.s. | q.s. | q.s. | q.s. | q.s. | q.s. |
| 2,4-Bis[5-1(dimethylpropyl)benzoxazol-2-yl-(4-phenyl)imino]-6-(2-ethylhexyl)imino-1,3,5-triazine | | 1.5 | | | | | | 9.4 | 8.2 |
| Aminobenzophenone | 1 | | | | | | | 6.7 | 8.9 |
| Octocrylene | | | | | | 10 | 10 | 10 | 10 |
| Terephthalidene Dicamphor Sulfonic Acid | | | | | | 8 | 9 | 9 | 9 |
| Drometrizole Trisiloxane | | | | | | 8 | 14 | 14 | 14 |
| Phenylbenzimidazole Sulfonic Acid | 2 | 2 | 2 | 2 | 2 | | | | |
| Disodium Phenyl Dibenzimidazole Tetrasulfonate | | 1.5 | | | | | | | |
| Diethylhexyl Butamido Triazone | 2 | 1 | 3 | 3 | 2 | | 5 | 5 | 5 |
| Bis-Ethylhexyloxyphenol Methoxyphenyl Triazine | 3 | 4 | 3 | 3 | 3 | | 3 | 3 | 3 |
| Ethylhexyl Triazone | 4 | 4 | 1.5 | 0.5 | 1.5 | | 2 | 2 | 2 |
| Butyl Methoxydibenzoylmethane | 4.0 | 3.0 | 4.5 | 4.5 | 4.5 | 4.9 | 4.5 | | 1 |
| Ethylhexyl Methoxycinnamate | 7.5 | 7.5 | 0 | 0 | 0 | | | | |
| Glycerol | 7.5 | 4 | 7.5 | 6 | 5 | 6 | 0 | 5 | 5 |
| Hydrogenated Coco-Glycerides | 1 | 0.5 | 1 | 0.5 | 0.6 | 0.5 | 0.6 | 0.6 | 0.6 |
| Dicaprylyl Carbonate | 1 | 2 | 3 | 4 | 2 | 4 | 2 | 2 | 2 |
| Butylene Glycol Dicaprylate/Dicaprate | 6.5 | 7.5 | 9 | 6 | 8 | 6 | 8 | 8 | 8 |
| C12–15 Alkyl Benzoate | 0 | 0 | 5 | 4 | 2 | 4 | 2 | 2 | 2 |
| Perfume | q.s. | q.s. | q.s. | q.s. | q.s. | q.s. | q.s. | q.s. | q.s. |
| Titanium Dioxide | 5 | 5 | 5 | 5 | 5 | 10 | 10 | 10 | 10 |
| Xanthan Gum | 0.2 | 0.4 | 0 | 0.3 | 0.1 | 0.3 | 0.1 | 0.1 | 0.1 |
| C18–36 Acid Triglyceride | 1 | 0.5 | 0 | 1 | 0.2 | 1 | 0.2 | 0.2 | 0.2 |
| Cetyl Alcohol | 1 | 1.5 | 1.2 | 0.5 | | 0.5 | | | |
| Aqua | ad 100 | ad 100 | ad 100 | ad 100 | ad 100 | ad 100 | ad 100 | ad 100 | ad 100 |
| Tocopheryl Acetate | 0.5 | 0.5 | 0.5 | 0.5 | 0.5 | 0.5 | 0.5 | 0.5 | 0.5 |
| Creatine | | 0.5 | | 0.5 | | | | | |
| Creatinine | | 0.05 | | 0.01 | | | | | |
| Taurine | 1 | | | 0.1 | | 0.1 | | | |

Sunsprays: Very High or Ultra High Protection, SPF 30/40/50/50+

| INCI | 1 | 2 | 3 | 4 | 5 | 6 | 7 | 8 |
|---|---|---|---|---|---|---|---|---|
| Alcohol Denat. | 2 | 3 | 0 | 5 | 4 | 5 | 4 | 5 |
| Ceteareth-20 | 0.5 | 1.5 | 1.2 | 1 | 1.2 | 1 | 1.2 | 1 |
| VP/Hexadecene Copolymer | 0.4 | 0.5 | 0.3 | 0.2 | 0.3 | 0.2 | 0.3 | 0.2 |
| Trisodium EDTA | 1 | 0 | 1 | 1 | 1.5 | 1 | 1 | 1 |
| Preservatives | q.s. | q.s. | q.s. | q.s. | q.s. | q.s. | q.s. | q.s. |
| Diethylhexyl Butamido Triazone | 2 | 0 | 2 | 2 | | | | |
| Disodium Phenyl Dibenzimidazole Tetrasulfonate | | 1 | | | | | 1.5 | |
| Phenylbenzimidazole Sulfonic Acid | 2 | 2 | 2 | 2 | | | | |
| Ethylhexyl Triazone | 3 | 3 | 0 | 0 | 5 | 0 | 5 | 0 |
| Bis-Ethylhexyloxyphenol Methoxyphenyl Triazine | 3 | 2.5 | 2 | 2 | | 2 | | 2 |
| Methylene Bis-Benztriazolyl Tetramethyl-butylphenol | | 3 | | | | 2.5 | | |
| Butyl Methoxydibenzoylmethane | 4.5 | 3.9 | 4.5 | 4.5 | 4.9 | 4.8 | 2 | |
| Ethylhexyl Methoxycinnamate | 0 | 6 | 3 | 3 | | 3 | | 3 |
| 2,4-Bis[5-1(dimethylpropyl)benzoxazol-2-yl-(4-phenyl)imino]-6-(2-ethylhexyl)imino-1,3,5-triazine | | 1 | | | | | 8.8 | 7.6 |
| Aminobenzophenone | 0.5 | | | | | | 9.6 | 8.4 |
| Octocrylene | 0 | 0 | 3 | 3 | 10 | 10 | 10 | 10 |
| Terephthalidene Dicamphor Sulfonic Acid | | | | | 7 | 9.8 | 7 | 9.8 |
| Drometrizole Trisiloxane | | | | | 8 | 11 | 8 | 11 |
| Glycerol | 7.5 | 5 | 6 | 6 | 6 | 6 | 6 | 6 |
| C12–15 Alkyl Benzoate | 3 | 0 | 0 | 0 | 0 | 0 | 0 | 0 |
| Butylene Glycol Dicaprylate/Dicaprate | 8 | 7 | 9 | 6 | 9 | 6 | 9 | 6 |
| Perfume | q.s. | q.s. | q.s. | q.s. | q.s. | q.s. | q.s. | q.s. |
| Titanium Dioxide | 0 | 0 | 2 | 1 | 10 | 7 | 10 | 7 |
| Acrylates/C10–30 Alkyl Acrylate Crosspolymer | 0.1 | 0.2 | 0.4 | 0.4 | 0.4 | 0.4 | 0.4 | 0.4 |
| C18–36 Acid Triglyceride | 1 | 1 | 1 | 1 | 1 | 1 | 1 | 1 |
| Aqua | ad 100 | ad 100 | ad 100 | ad 100 | ad 100 | ad 100 | ad 100 | ad 100 |

-continued

| INCI | 1 | 2 | 3 | 4 | 5 | 6 | 7 | 8 |
|---|---|---|---|---|---|---|---|---|
| Creatinine | 0.05 | 0.05 | 0 | 0 | 0 | 0.05 | 0 | 0.05 |
| Tocopheryl Acetate | 0.5 | 0.5 | 0.5 | 0.5 | 0.5 | 0.5 | 0.5 | 0.5 |
| Taurine | | 1.1 | | 0.8 | | | | |
| Creatine | 0.2 | 0.5 | 0 | 0 | 0 | 0 | 0 | 0 |
| Panthenol | 0 | 0 | 1.4 | 1.4 | 1.4 | 1.4 | 1.4 | 1.4 |

O/W Emulsions: Very High Protection SPF 30/40

| INCI | 1 | 2 | 3 | 4 | 5 | 6 |
|---|---|---|---|---|---|---|
| Alcohol Denat. | 3 | 0 | 5 | 2 | 5 | 5 |
| Acrylates/C10–30 Alkyl Acrylate Crosspolymer | 0.02 | 0.05 | 0 | 0.05 | 0 | 0 |
| Polyglyceryl-2 Dipolyhydroxystearate | 0.4 | 0.5 | 0 | 0.5 | 0 | 0 |
| Glyceryl Stearate Citrate | 1.5 | 2.5 | 0 | 2.5 | 0 | 0 |
| Glyceryl Stearate SE | 0 | 0 | 1 | 0 | 1 | 1 |
| Cetearyl Alcohol + PEG-40 Castor Oil + Sodium Cetearyl Sulfate | 0 | 0 | 2.5 | 0 | 2.5 | 2.5 |
| VP/Hexadecene Copolymer | 0.5 | 0.5 | 0.5 | 0.5 | 0.5 | 0.5 |
| Trisodium EDTA | 1 | 1 | 1 | 1 | 1 | 1 |
| Preservatives | q.s. | q.s. | q.s. | q.s. | q.s. | q.s. |
| Terephthalidene Dicamphor Sulfonic Acid | | | | 8 | 10 | 10 |
| Drometrizole Trisiloxane | | | | 10 | 12 | 12 |
| Ethylhexyl Triazone | 1.5 | 4 | 0 | | | |
| Disodium Phenyl Dibenzimidazole Tetrasulfonate | 1 | | | | 1.2 | |
| Bis-Ethylhexyloxyphenol Methoxyphenyl Triazine | 2.5 | 2.5 | 2.5 | | | |
| Methylene Bis-Benztriazolyl Tetramethylbutylphenol | | 1.5 | | | | 2 |
| Butyl Methoxydibenzoylmethane | 4 | 4.5 | 4 | 4.8 | 4.9 | |
| Ethylhexyl Methoxycinnamate | 9 | 0 | 6 | | | |
| Diethylhexyl Butamido Triazone | 0 | 1 | 0 | 1 | | |
| Phenylbenzimidazole Sulfonic Acid | 0 | 0 | 2 | | | |
| 2,4-Bis[5-1(dimethylpropyl)benzoxazol-2-yl-(4-phenyl)imino]-6-(2-ethylhexyl)imino-1,3,5-triazine | | | | 1.5 | | 9.2 |
| Hexyl 2-(4'-diethylamino-2-hydoxybenzoyl)benzoate | 1 | | | | | 8.6 |
| Octocrylene | 0 | 0 | 3 | 10 | 10 | 10 |
| Ethylhexylglycerol | 0.2 | 0.5 | 0.4 | 0.5 | 0.4 | 0.4 |
| Glycerol | 7.5 | 5 | 7.5 | 5 | 7.5 | 7.5 |
| Hydrogenated Coco-Glycerides | 1 | 1 | 1 | 1 | 1 | 1 |
| Dicaprylyl Ether | 1 | 4 | 2 | 4 | 2 | 2 |
| C12–15 Alkyl Benzoate | 2 | 5 | 4 | 5 | 4 | 4 |
| Butylene Glycol Dicaprylate/Dicaprate | 2.5 | 6.5 | 3 | 6.5 | 3 | 3 |
| Dibutyl Adipate | 0 | 0 | 2 | 0 | 2 | 2 |
| Perfume | q.s. | q.s. | q.s. | q.s. | q.s. | q.s. |
| Titanium Dioxide | 3 | 3 | 3 | 6 | 6 | 6 |
| Dihydroxyacetone (DHA) | 3 | | 1 | | | |
| Cyclomethicone | 0 | 2 | 0 | 2 | 0 | 0 |
| Xanthan Gum | 0.2 | 0.3 | 0.4 | 0.3 | 0.4 | 0.4 |
| Stearyl Alcohol | 1.5 | 1 | 1 | 1 | 1 | 1 |
| Aqua | ad 100 | ad 100 | ad 100 | ad 100 | ad 100 | ad 100 |
| Creatinine | 0.05 | 0.04 | 0.05 | 0.04 | 0.05 | 0.05 |
| Taurine | 0.9 | | | | | |
| Tocopheryl Acetate | 0.5 | 0.5 | 0.5 | 0.5 | 0.5 | 0.5 |
| Creatine | 0.5 | 0.4 | 0.5 | 0.4 | 0.5 | 0.5 |
| Vitamin A- Palmitate | | | 0.2 | 0.2 | | |

W/O Emulsions with Low Viscosity: Very High Protection SPF 30/40/50

| INCI | 1 | 2 |
|---|---|---|
| Alcohol Denat. | 3 | 2 |
| PEG-45/Dodecyl Glycol Copolymer | 0.5 | 1 |
| Cetyl PEG/PPG-10/1 Dimethicone | 1.0 | 1.5 |
| Polyglyceryl-2 Dipolyhydroxystearate | 1 | 2 |
| Trisodium EDTA | 0.5 | 1 |
| Preservatives | q.s | q.s |
| Diethylhexyl Butamido Triazone | 1.5 | 2 |
| Bis-Ethylhexyloxyphenol Methoxyphenyl Triazine | 2 | 3 |
| Ethylhexyl Triazone | 4 | 3 |
| Butyl Methoxydibenzoylmethane | 4.5 | 4.0 |
| Phenylbenzimidazole Sulfonic Acid | 0 | 1 |
| Ethylhexyl Methoxycinnamate | 0 | 7 |
| Glycerol | 6 | 4 |
| Dibutyl Adipate | 5 | 2.5 |
| Butylene Glycol Dicaprylate/Dicaprate | 7 | 8.5 |
| C12–15 Alkyl Benzoate | 6 | 9 |
| Perfume | 0.4 | 0.4 |
| Titanium Dioxide + Trimethoxycaprylylsilane | 2 | 3 |
| Magnesium Sulfate | 0.3 | 0.1 |
| Cyclomethicone | 10 | 14 |
| Aqua | ad 100 | ad 100 |
| Tocopheryl Acetate | 0.3 | 0.3 |

The invention claimed is:

1. A cosmetic preparation, wherein the preparation comprises at least one UV filter substance, exhibits a UVA balance of higher than 15, and further comprises one or more of creatine, creatinine, taurine, ubiquinol, ubiquinone, folic acid, 8-hexadecene-1,16-dicarboxylic acid, biotin, isoflavone, a licochalcone, silymarin, silyphos, an extract of licorice, dihydroxyacetone, erythrulose and/or further comprises from 1% to 30% by weight of glycerol, based on a total weight of the preparation.

2. The preparation of claim 1, wherein the preparation exhibits a UVA balance of higher than 22.

3. The preparation of claim 1, wherein the preparation exhibits a UVA balance of higher than 30.

4. The preparation of claim 1, wherein the preparation exhibits a UVA balance of higher than 40.

5. The preparation of claim 1, wherein the at least one UV filter substance is selected from water-soluble UV filters, UV filters which are liquid at room temperature, organic pigments, inorganic pigments, and broadband filters.

6. The preparation of claim 5, wherein the at least one UV filter substance comprises at least one triazine compound.

7. The preparation of claim 5, wherein the at least one UV filter substance comprises one or more water-soluble UVA filter substances.

8. The preparation of claim 1, wherein the preparation comprises at least one UV filter substance which is selected from benzoxazole compounds and hydroxybenzophenones.

9. The preparation of claim 1, wherein the preparation exhibits a sun protection factor, determined in accordance with COLIPA method, of at least 20.

10. The preparation of claim 2, wherein the preparation exhibits a sun protection factor, determined in accordance with COLIPA method, of at least 30.

11. The preparation of claim 1, wherein the preparation comprises from 1% to 10% by weight of glycerol, based on a total weight of the preparation.

12. The preparation of claim 1, wherein the preparation comprises one or more of creatine, creatinine, taurine, ubiquinol, ubiquinone, folic acid, 8-hexadecene-1,16-dicarboxylic acid, biotin, isoflavone, licochalcones, silymarin, silyphos, extracts of licorice, dihydroxyacetone, and erythrulose.

13. The preparation of claim 1, wherein the preparation comprises at least one of creatine and creatinine.

14. The preparation of claim 1, wherein the preparation comprises taurine.

15. The preparation of claim 1, wherein the preparation comprises at least one of creatine, creatinine and taurine in a total concentration of from 0.1% to 2% by weight, based on a total weight of the preparation.

16. The preparation of claim 1, wherein the preparation comprises at least one of phenylene-1,4-bis(2-benzimidazyl)-3,3'-5,5'-tetrasulfonic acid, 2,4-bis[5-1(dimethylpropyl)benzoxazol-2-yl(4-phenyl)imino]-6-(2-ethylhexyl)imino-1,3,5-triazine, and hexyl 2-(4'-diethylamino-2'-hydoxybenzoyl)benzoate.

17. The preparation of claim 1, wherein the preparation comprises at least 0.5% by weight, based on a total weight of the preparation, of at least one organic broadband filter.

18. The preparation of claim 17, wherein the at least one organic broadband filter is selected from asymmetrically substituted s-triazine compounds and benzotriazoles.

19. The preparation of claim 18, wherein the preparation comprises 2,4-bis{[4-(2-ethylhexyloxy)-2-hydroxy]phenyl}-6-(4-methoxyphenyl)-1,3,5-triazine.

20. The preparation of claim 1, wherein the preparation provides an independent Endogenous Protection Factor ($EPF_{ind}$) of greater than 1.5.

21. The preparation of claim 1, wherein the preparation exhibits a UVA balance of higher than 22 and a sun protection factor, determined in accordance with COLIPA method, of at least 20.

22. The preparation of claim 1, wherein the preparation exhibits a UVA balance of higher than 30 and a sun protection factor, determined in accordance with COLIPA method, of at least 30.

23. A cosmetic preparation, wherein the preparation comprises at least one UV filter substance and exhibits a UVA balance of higher than 15, the at least one UV filter substance comprising at least 0.5% by weight, based on a total weight of the preparation, of at least one organic broadband filter.

24. The preparation of claim 23, wherein the preparation exhibits a UVA balance of higher than 22.

25. The preparation of claim 23, wherein the preparation exhibits a UVA balance of higher than 30.

26. The preparation of claim 23, wherein the preparation exhibits a sun protection factor, determined in accordance with COLIPA method, of at least 20.

27. The preparation of claim 25, wherein the preparation exhibits a sun protection factor, determined in accordance with COLIPA method, of at least 30.

28. The preparation of claim 23, wherein the preparation provides an independent Endogenous Protection Factor ($EPF_{ind}$) of greater than 1.5.

29. The preparation of claim 23, wherein the at least one organic broadband filter is selected from asymmetrically substituted s-triazine compounds and benzotriazoles.

30. The preparation of claim 29, wherein the preparation comprises 2,4-bis{[4-(2-ethylhexyloxy)-2-hydroxy]phenyl}-6-(4-methoxyphenyl)-1,3,5-triazine.

31. The preparation of claim 23, wherein the preparation further comprises one or more of glycerol, creatine, creatinine, taurine, ubiquinol, ubiquinone, folic acid, 8-hexadecene-1,16-dicarboxylic acid, biotin, isoflavone, a licochalcone, silymarin, silyphos, an extract of licorice, dihydroxyacetone, erythrulose.

* * * * *